(12) United States Patent
Full

(10) Patent No.: US 9,101,562 B2
(45) Date of Patent: Aug. 11, 2015

(54) ADDITIVES FOR CHLORINE DIOXIDE-CONTAINING COMPOSITIONS

(75) Inventor: Andrew Patrick Full, Fanwood, NJ (US)

(73) Assignee: BASF CORPORATION, Florham Park, NJ (US)

(*) Notice: Subject to any disclaimer, the term of this patent is extended or adjusted under 35 U.S.C. 154(b) by 330 days.

(21) Appl. No.: 13/017,096

(22) Filed: Jan. 31, 2011

(65) Prior Publication Data

US 2011/0189112 A1    Aug. 4, 2011

Related U.S. Application Data

(60) Provisional application No. 61/299,999, filed on Jan. 31, 2010.

(51) Int. Cl.
| | |
|---|---|
| *A61K 8/20* | (2006.01) |
| *A61K 8/73* | (2006.01) |
| *A61Q 11/00* | (2006.01) |
| *A61K 31/045* | (2006.01) |
| *A61K 31/11* | (2006.01) |
| *A61K 31/135* | (2006.01) |
| *A61K 31/352* | (2006.01) |

(52) U.S. Cl.
CPC ............ *A61K 31/045* (2013.01); *A61K 8/20* (2013.01); *A61K 31/11* (2013.01); *A61K 31/135* (2013.01); *A61K 31/352* (2013.01); *A61Q 11/00* (2013.01)

(58) Field of Classification Search
CPC .......... A61K 8/22; A61K 8/463; A61O 11/00
USPC ................................... 424/406, 49
See application file for complete search history.

(56) References Cited

U.S. PATENT DOCUMENTS

| | | | |
|---|---|---|---|
| 2,071,091 A | 2/1937 | Taylor | |
| 3,953,566 A | 4/1976 | Gore | |
| 4,060,600 A | 11/1977 | Vit | |
| 4,104,190 A | 8/1978 | Hartshorn | |
| 4,330,531 A | 5/1982 | Alliger | |
| 4,585,482 A | 4/1986 | Tice | |
| 4,683,039 A | 7/1987 | Twardowski | |
| 4,689,215 A | 8/1987 | Ratcliff | |
| 4,692,262 A * | 9/1987 | Brown et al. ............... | 510/131 |
| 4,696,811 A | 9/1987 | Ratcliff | |
| 4,731,192 A * | 3/1988 | Kenjo et al. ............... | 510/113 |
| 4,786,492 A | 11/1988 | Ratcliff | |
| 4,788,053 A | 11/1988 | Ratcliff | |
| 4,792,442 A | 12/1988 | Ratcliff | |
| 4,793,989 A | 12/1988 | Ratcliff | |
| 4,808,389 A | 2/1989 | Ratcliffe | |
| 4,818,519 A | 4/1989 | Ratcliff | |
| 4,832,009 A | 5/1989 | Dillon | |
| 4,837,009 A | 6/1989 | Ractliff | |
| 4,851,213 A | 7/1989 | Ratcliff | |
| 4,855,135 A | 8/1989 | Ratcliff | |
| 4,865,848 A | 9/1989 | Cheng | |
| 4,886,657 A | 12/1989 | Ratcliff | |
| 4,889,714 A | 12/1989 | Ratcliff | |
| 4,925,656 A | 5/1990 | Ratcliff | |
| 4,945,125 A | 7/1990 | Dillon | |
| 4,975,285 A | 12/1990 | Ratcliff | |
| 5,200,171 A | 4/1993 | Ratcliff | |
| 5,227,168 A | 7/1993 | Chvapil | |
| 5,281,412 A | 1/1994 | Lukacovic | |
| 5,348,734 A | 9/1994 | Ratcliff | |
| 5,399,288 A | 3/1995 | Marzouk | |
| 5,407,656 A | 4/1995 | Roozdar | |
| 5,489,435 A | 2/1996 | Ratcliff | |
| 5,597,561 A | 1/1997 | Kross | |
| 5,616,347 A | 4/1997 | Alliger et al. | |
| 5,618,550 A | 4/1997 | Ratcliff | |
| 5,648,074 A * | 7/1997 | Park et al. ................... | 424/94.2 |
| 5,651,996 A | 7/1997 | Roozdar | |
| 5,719,100 A | 2/1998 | Zahradnik | |
| 5,753,217 A * | 5/1998 | Christopfel ................. | 424/76.9 |
| 5,820,822 A | 10/1998 | Kross | |
| 5,879,691 A | 3/1999 | Sagel | |
| 5,914,120 A * | 6/1999 | Wellinghoff et al. ........ | 424/406 |
| 5,944,528 A | 8/1999 | Montgomery | |
| 5,980,923 A | 11/1999 | Dillon | |
| 6,007,735 A | 12/1999 | Creed | |
| 6,039,934 A | 3/2000 | Alliger | |
| 6,046,243 A | 4/2000 | Wellinghoff | |
| 6,077,495 A | 6/2000 | Speronello | |
| 6,077,502 A | 6/2000 | Witt | |

(Continued)

FOREIGN PATENT DOCUMENTS

| | | |
|---|---|---|
| CA | 955848 | 10/1974 |
| DE | 19854349 A1 | 5/2000 |
| WO | WO 2007/062347 A2 | 5/2007 |
| WO | WO 2007/079287 A2 | 7/2007 |
| WO | WO 2007/131970 A1 | 11/2007 |

OTHER PUBLICATIONS

International Search Report dated Oct. 10, 2011 issued for PCT/US2011/023093.
Alliger, Howard. 'Overview of Chlorine Dioxide ($ClO_2$)' [online] [retrieved Aug. 24, 2011] Retrieved from the Internet:<http://www.grandcircuitinc.com/Howard%20Alliger%20%20An%20Overall%20View%20Cl02.pdf>.
International Preliminary Report on Patentability issued Jul. 31, 2012 for International Application No. PCT/US2011/023093 filed Jan. 31, 2011.

*Primary Examiner* — Walter Webb

(74) *Attorney, Agent, or Firm* — Drinker Biddle & Reath LLP

(57) ABSTRACT

Provided is a composition containing chlorine dioxide, a vehicle and at least one compatible additive. The composition optionally contains a compatible amount of a non-compatible additive. Methods of making and using the composition are also provided.

20 Claims, 17 Drawing Sheets

(56) References Cited

U.S. PATENT DOCUMENTS

| | | |
|---|---|---|
| 6,106,284 A | 8/2000 | Cronin |
| 6,238,643 B1 | 5/2001 | Thangaraj |
| 6,280,716 B1 | 8/2001 | Ratcliff |
| 6,280,775 B1 | 8/2001 | Sasson |
| 6,287,551 B1 | 9/2001 | Ratcliff |
| 6,294,108 B1 | 9/2001 | Speronello |
| 6,294,510 B1 | 9/2001 | Norman |
| 6,312,670 B1 | 11/2001 | Montgomery |
| 6,375,933 B1 * | 4/2002 | Subramanyam et al. ....... 424/49 |
| 6,379,658 B1 | 4/2002 | Marano |
| 6,425,759 B1 | 7/2002 | Cronin |
| 6,432,322 B1 | 8/2002 | Speronello |
| 6,432,387 B1 | 8/2002 | Laizuka |
| 6,479,037 B1 | 11/2002 | Montgomery |
| 6,500,408 B2 | 12/2002 | Chen |
| 6,524,624 B1 | 2/2003 | Morelli et al. |
| 6,551,579 B2 | 4/2003 | Sagel |
| 6,582,682 B2 | 6/2003 | Stier |
| 6,669,931 B2 | 12/2003 | Lynch |
| 6,682,721 B2 | 1/2004 | Kim |
| 6,699,404 B2 | 3/2004 | Speronello |
| 6,759,030 B2 | 7/2004 | Kosti |
| 6,848,905 B2 | 2/2005 | Jacobs |
| 6,881,061 B2 | 4/2005 | Fisher |
| 6,896,518 B2 | 5/2005 | Jacobs |
| 6,964,571 B2 | 11/2005 | Andersen |
| 7,004,756 B2 | 2/2006 | Andersen |
| 7,029,705 B2 | 4/2006 | Fuhr |
| 7,040,897 B2 | 5/2006 | Fischer |
| 7,044,737 B2 | 5/2006 | Fu |
| 7,087,190 B2 | 8/2006 | Hei |
| 7,087,208 B2 | 8/2006 | Sampson |
| 7,182,883 B2 | 2/2007 | Speronello |
| 7,220,367 B2 | 5/2007 | Speronello |
| 7,229,647 B2 | 6/2007 | Lee |
| 7,273,567 B1 | 9/2007 | Wellinghoff |
| 7,384,650 B2 | 6/2008 | Chien |
| 7,514,019 B2 | 4/2009 | Martin |
| 7,534,368 B2 | 5/2009 | Martin |
| 8,021,694 B2 | 9/2011 | Morelli et al. |
| 2003/0152528 A1 | 8/2003 | Singh |
| 2003/0235549 A1 | 12/2003 | Singh |
| 2005/0142215 A1 | 6/2005 | Kling |
| 2006/0024369 A1 | 2/2006 | Speronello |
| 2006/0045855 A1 | 3/2006 | Sasson |
| 2006/0088498 A1 | 4/2006 | Martin |
| 2006/0099550 A1 | 5/2006 | Faasse |
| 2006/0169949 A1 | 8/2006 | Speronello |
| 2006/0183080 A1 | 8/2006 | Nosov |
| 2006/0223033 A1 | 10/2006 | McLean |
| 2006/0292090 A1 | 12/2006 | Sharma |
| 2007/0172412 A1 | 7/2007 | Hratko |
| 2007/0202095 A1 | 8/2007 | Speronello |
| 2007/0231277 A1 | 10/2007 | Sharma |
| 2007/0298380 A1 | 12/2007 | Allred |
| 2008/0023668 A1 | 1/2008 | Callerame |
| 2008/0025925 A1 | 1/2008 | Allred |
| 2008/0041400 A1 | 2/2008 | Darnell |
| 2008/0208179 A1 | 8/2008 | Chan |
| 2008/0209650 A1 | 9/2008 | Brewer |
| 2009/0016973 A1 | 1/2009 | Ratcliff |
| 2010/0012891 A1 | 1/2010 | Speronello |
| 2010/0012892 A1 | 1/2010 | Speronello |
| 2010/0012893 A1 | 1/2010 | Speronello |
| 2010/0012894 A1 | 1/2010 | Speronello |
| 2010/0015066 A1 | 1/2010 | Speronello |
| 2010/0015067 A1 | 1/2010 | Speronello |
| 2010/0062042 A1 | 3/2010 | Speronello |
| 2010/0062043 A1 | 3/2010 | Speronello |
| 2010/0062076 A1 | 3/2010 | Speronello |
| 2010/0112059 A1 | 5/2010 | Speronello |

* cited by examiner

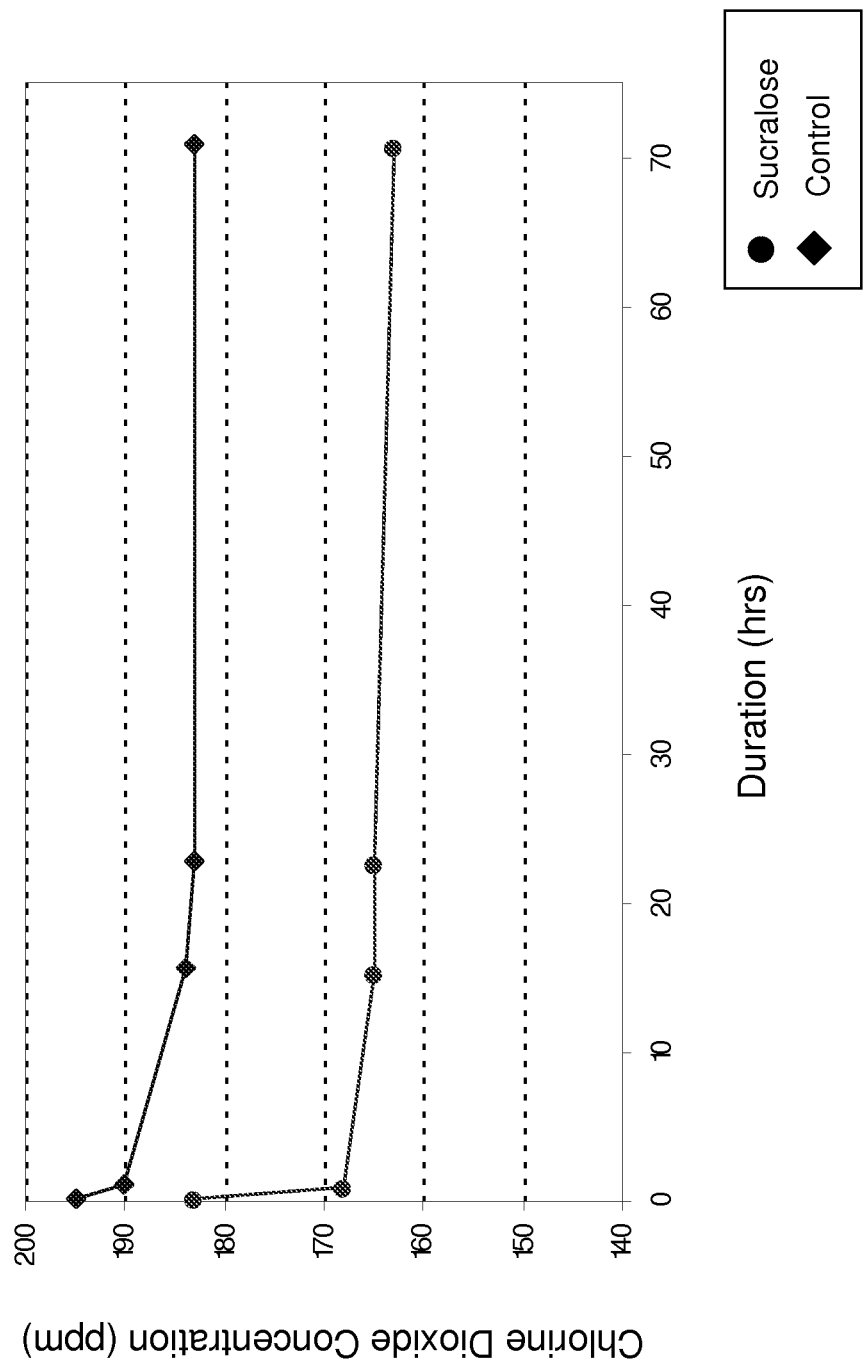

L-menthol

Benzaldehyde

Camphor

Menthone

Ethyl Menthane Carboxamide

Eucalyptol

Aspartame

Sodium Cyclamate

Sodium Saccharin Dihydrate

Cetylpyridinium Chloride

Sucralose

Sodium Bisulfate

Benzyl Alcohol

Propylene Glycol

Polyethylene Glycol 400

Glycerol

Ethyl Acetate

Ethanol

Hydroxypropyl Methylcellulose

Acetone

Glycine l-Glutamic acid

Boric Acid

Citric Acid

Potassium Acetate

T-Cinnamaldehyde

Furaneol

Ascorbic Acid

Sorbic Acid

Methyl Vanillin

Anethole

Acesulfame Potassium

Phenol

Sodium Propionate

Potassium Sorbate

Sodium Carboxymethylcellulose

Triethanolamine

Monoethanolamine

Sodium Carbonate

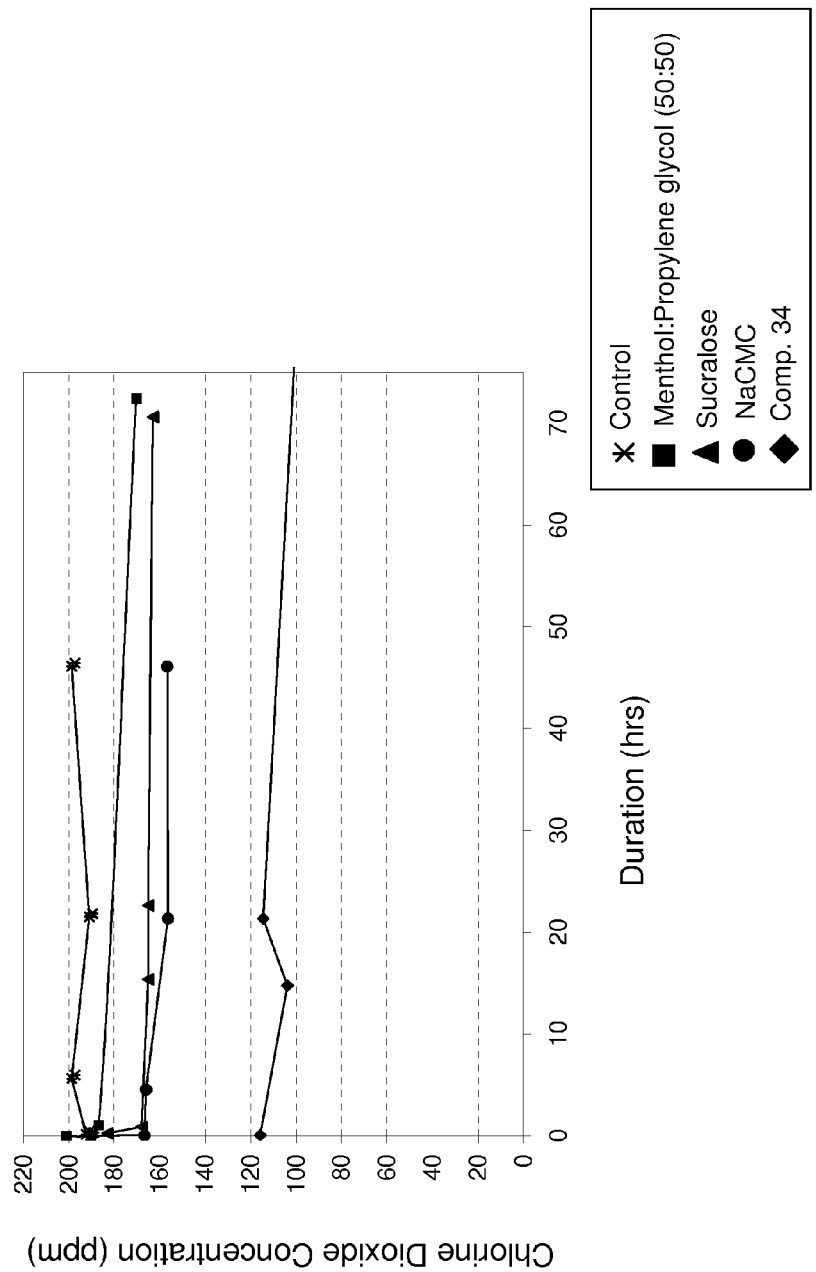

ADDITIVES FOR CHLORINE DIOXIDE-CONTAINING COMPOSITIONS

CROSS-REFERENCE TO RELATED APPLICATIONS

This application claims the benefit pursuant to 35 U.S.C. §119(e) of U.S. Provisional Application No. 61/299,999, filed on Jan. 31, 2010, which is hereby incorporated by reference in its entirety herein.

BACKGROUND

Chlorine dioxide is a strong oxidizing agent. The bactericidal, algaecidal, fungicidal, bleaching, and deodorizing properties of chlorine dioxide are well known. Applications making use of such properties include, but are not limited to, oral care, wound care, hard surface cleansing or disinfection, treatment of fungal infections of toenail, fingernail, and/or skin, and the like.

Chlorine dioxide compositions for these diverse applications typically comprise additional components to provide additional properties or functions. Such properties or functions are influenced by the intended use of the composition. For instance, compositions intended for oral cosmetic and/or therapeutic applications can further comprise components that include, but are not limited to, sweeteners, flavorants, encapsulates, coloring agents and fragrances. Additional components for a composition intended for oral cosmetic and/or therapeutic use can include: antibacterial agents (in addition to chlorine dioxide), enzymes, malodor controlling agents (in addition to chlorine dioxide), cleaning agents, such as phosphates, antigingivitis agents, antiplaque agents, antitartar agents, anticaries agents such as a source of fluoride ion, antiperiodontitis agents, nutrients, antioxidants, surfactants, plasticizers, and the like. Components for a composition intended for topical disinfectant of a hard surface can include: fragrance, coloring agent such as a pigment or a dye, surfactants, effervescing agents, cleaning agents such as sodium lauryl sulfate, anti-corrosion agents, and the like. For topical disinfectant of a biological tissue, optional ingredients can include: fragrance, coloring agents, local anesthetics such as menthol, chloroform, and benzocaine, emollients or moisturizers, analgesics, UV absorbers, surfactants, plasticizers, cleaning agents such as sodium lauryl sulfate, antibacterial agents (in addition to chlorine dioxide), malodor controlling agents (in addition to chlorine dioxide), bioadhesive polymers such as polycarbophil, polyvinylpyrrolidone, or a mixture thereof.

Generally, each category of component contains numerous examples. For instance, sweeteners include aspartame, acesulfame potassium, sodium cyclamate, sodium saccharin dihydrate, sucralose, and sugar alcohols. Exemplary sugar alcohols include sorbital, xylitol, lactitol, mannitol, maltitol, hydrogenated starch hydrolysate, erythritol, reducing paratinose and mixtures thereof. Flavoring agents include, e.g., natural or synthetic essential oils, as well as various flavoring aldehydes, esters, alcohols, and other materials. Examples of essential oils include oils of spearmint, peppermint, wintergreen, sassafras, clove, sage, eucalyptus, marjoram, cinnamon, lemon, lime, grapefruit, and orange. Other flavoring agents include leaf alcohol, anethole, methyl salicylate, cassia, 1-8 methyl acetate, eugenol, oxanone, α-irisone, propenyl guaethol, thymol, and cinnamaldehyde glycerol acetal. Flavor agents also frequently comprise blends of individual flavor agents as well.

Fragrances include menthol, menthyl acetate, menthyl lactate, camphor, eucalyptus oil, eucalyptol, anethole, eugenol, cassia, oxanone, α-irisone, propenyl guaethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like.

Coloring agents include, for example, organic and inorganic pigments and FD&C or D&C pigments and dyes approved by the FDA for use in the United States. Organic pigments are generally various aromatic types including azo, indigoid, triphenylmethane, anthraquinone, and xanthine dyes which are designated as D&C and FD&C blues, browns, greens, oranges, reds, yellows, etc., such as FD&C Blue No. 1, FD&C Green No. 3, FD&C Red No. 40, FD&C Yellow No. 5, D&C Orange No. 4, D&C Red No. 27, and D&C Violet No. 2. Inorganic pigments include iron oxides, ultramarines, chromium, chromium hydroxide colors, such as manganese violet, ultramarine blue, cosmetic red oxide, chromium green oxide, iron oxide yellow, and titanium dioxide, and mixtures thereof.

Surfactants known in the art include but are not limited to amphoteric surfactants, anionic surfactants, cationic surfactants and nonionic surfactants. Examples of amphoteric surfactants include propionates, alkyldimethyl betaines, alkylamido betaines, sulfobetaines, and imidazoline. Examples of anionic surfactants include fatty alcohol sulfates, alpha olefin sulfonates, sulfosuccinates, phosphate esters, carboxylates and sarcosinates. Examples of cationic surfactants include alkyl quaternaries, alylamido quaternaries, and imidazoline quaternaries. Examples of nonionic ionic surfactants include alkanolamides, ethoxylated amides, esters, alkoxylated alcohols, alkoxylated triglycerides, alkylpolyglucosides, amine oxides, sorbitan esters, and ethoxylates. Surfactants also include silicone surfactants such as dimethicone copolyols, alkyl dimethicone copolyols, silicone quaternary compounds, silicone phosphate esters, and silicone esters. Anti-tartar agents include but are not limited to, polyphosphates and salts thereof, polyamino propane sulfonic acid (AMPS) and salts thereof, polyolefin sulfonates and salts thereof, polyvinyl phosphates and salts thereof, diphosphonates and salts thereof, phosphonoalkane carboxylic acid and salts thereof, and polyphosphonates and salts thereof.

Thus, there are a myriad of possible additive types, with a plethora of examples for each type.

Chlorine dioxide, being a strong oxidizing agent, is a reactive molecule. Accordingly, chlorine dioxide can react with an additive in a composition. This unintended consequence causes the loss of chlorine dioxide, thus reducing the efficacy of the chlorine dioxide containing composition for its intended purpose. It can also lead to the generation of cytotoxic levels of oxy-chlorine anion in the composition, which is undesirable in compositions intended for contact with biological tissues.

Compositions comprising chlorine dioxide and additives that do not react with chlorine dioxide are needed. The present disclosure meets and addresses these needs.

SUMMARY

Provided is a composition consisting of chlorine dioxide, a vehicle, at least one compatible additive and optionally a compatible amount of at least one non-compatible additive. Compatible additives can have a chemical structure selected from the group consisting of a saturated hydrocarbon, a cyclic hydrocarbon, an aromatic, a non-ionized non-aromatic carboxylic acid, an amine, an ether, an aldehyde, a ketone, an alcohol, a quaternary ammonium salt and combinations thereof. Exemplary compatible additives include, but are not limited to, L-menthol, benzaldehyde, camphor, methone, ethyl menthane carboxamide, eucalyptol, aspartame, sodium cyclamate, sodium saccharin dihydrate, sucralose, cetylpyridinium chloride, benzoyl alcohol, propylene glycol, polyethylene glycol 400, glycerol, ethyl acetate, ethanol, hydroxypropyl methylcellulose, acetone, glycine, 1-glutamic acid, boric acid, citric acid and sodium bisulfate.

A method of preparing a chlorine-dioxide containing the composition containing a compatible additive is also provided. The steps of the method comprise combining a chlorine dioxide precursor, at least one compatible additive, optionally a compatible amount of a non-compatible additive, and a vehicle.

Also provided is a method of whitening a tooth surface. The method comprises contacting a surface of a tooth with an efficacious amount of the composition composition consisting of chlorine dioxide, a vehicle, at least one compatible additive and optionally a compatible amount of at least one non-compatible additive. The contacting step can be iterative. In an embodiment, the iterations are substantially contiguous. In an embodiment, the iterations are separated by at least about 12 hours. In an embodiment, contacting the tooth surface with the composition does not: substantially damage hard tooth tissue, substantially reduce enamel microhardness, substantially reduce dentin microhardness, cause tooth sensitivity, and/or substantially increase surface roughness of at least one of enamel and dentin. In an embodiment, the contacted tooth surface is whitened by at least about 1 shade value unit.

Embodiments of the composition and methods can include the following.

In an embodiment, the composition can comprise about 0.5 parts-per-million (ppm) to about 1000 ppm chlorine dioxide in one aspect.

In an embodiment, the composition has an ionic strength of at least about 5% of the chlorine dioxide in the composition.

In an embodiment, the at least one compatible additive does not comprise a conjugated double bond, an oxygen atom adjacent to aromatic rings, an ionized salt of carboxylic acid, an amino-ethanol or an inorganic carbonate salt.

In an embodiment, a non-compatible additive is present and is a thickener. The thickener can be sodium carboxymethylcellulose.

The at least one compatible additive can be selected from the group consisting of: a sweetener, a carrier, a flavor agent, an antiseptic, a preservative, a pigment, a fragrance, a plasticizer, an encapsulate, an antitartar agent, a surfactant, a buffer, and a cleaning agent.

In another embodiment, the at least one compatible additive in the composition is selected from the group consisting of: a sweetener, a carrier, a flavor agent, an antiseptic and a preservative, and the composition optionally includes a compatible amount of a non-compatible additive is present, wherein the non-compatible additive is a thickener.

In an embodiment, the at least one compatible additive is a first compatible additive and a second compatible additive. The first compatible additive can be a sweetener and the second compatible additive can be a flavor agent. In an embodiment, the sweetener is present at about 0.5 wt. % to about 1.0 wt. % and the flavor agent is present at about 0.4 wt. % to about 1.1 wt. %.

In an embodiment, the composition comprising a first compatible additive and a second compatible additive can further comprise a non-compatible additive. In an embodiment, the non-compatible additive can be sodium carboxymethylcellulose.

It is to be understood that both the foregoing general description and the following detailed description are exemplary and explanatory and are intended to provide further explanation of the subject matter as claimed.

BRIEF DESCRIPTION OF THE DRAWINGS

For the purpose of illustrating the various compositions and methods, there are depicted in the drawings certain embodiments. However, the compositions and their methods of use are not limited to the precise arrangements and instrumentalities of the embodiments depicted in the drawings.

FIGS. 1A and 1B depict graphs of chlorine dioxide ($ClO_2$) concentration as a function of time for 200 parts-per-million (ppm) $ClO_2$ compositions comprising a single sweetener additive at 0.5 wt. % or no additive (control). FIG. 1A depicts data for five different sweeteners and the control. FIG. 1B depicts the sucralose and control data only.

FIG. 4 depicts a graph of chlorine dioxide ($ClO_2$) concentration as a function of time for a series of 200 ppm $ClO_2$ compositions comprising one of two individual compatible additives (L-menthol and sucralose) or a compatible amount of a non-compatible additive (sodium carboxymethycellulose; "NaCMC"), as well as a 200 ppm $ClO_2$ composition containing all three additives ("Comp 34"). Data for a control composition, comprising on 200 ppm $ClO_2$ in water is also shown.

DETAILED DESCRIPTION

Figure 1A:
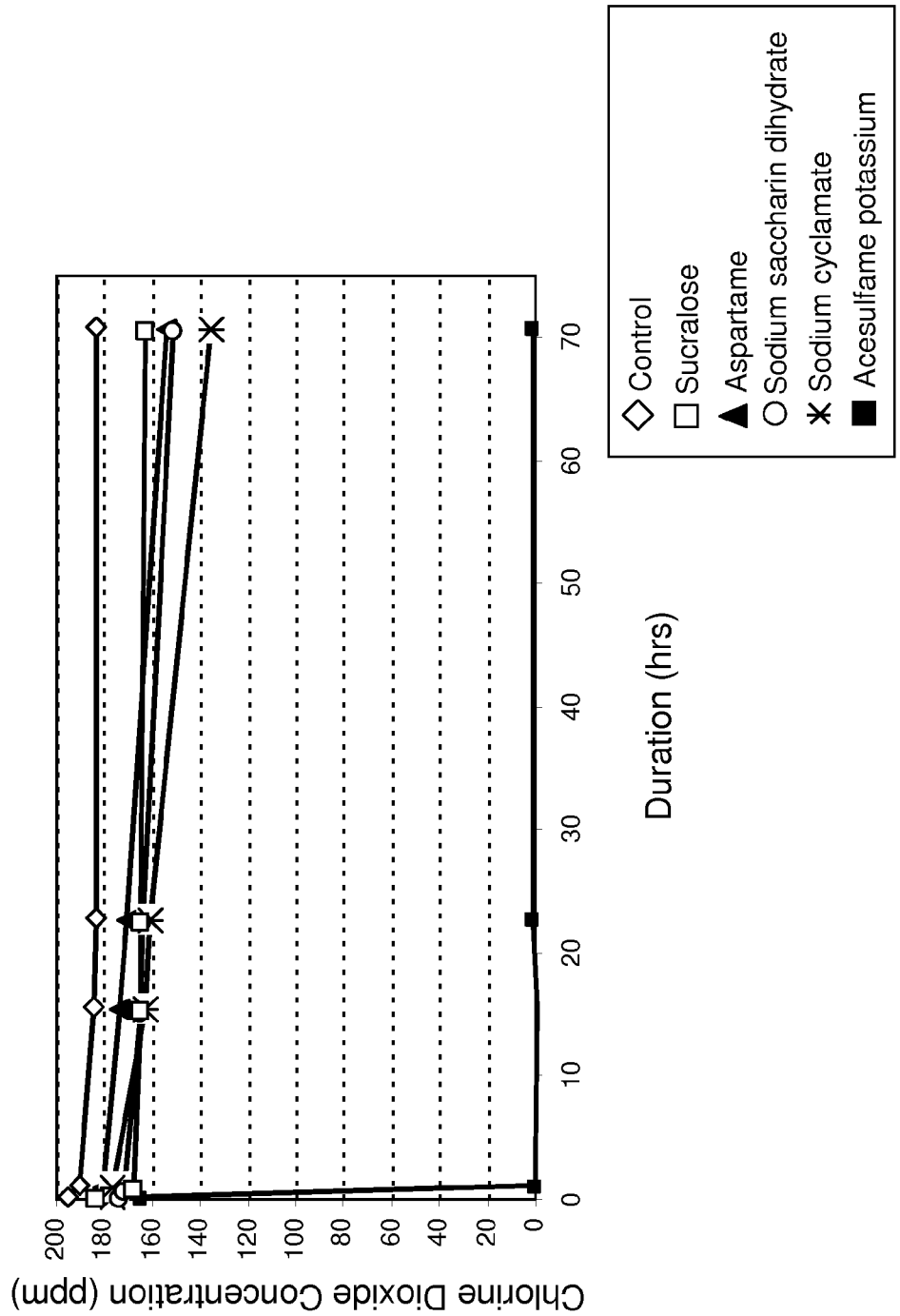
Figure 2A:
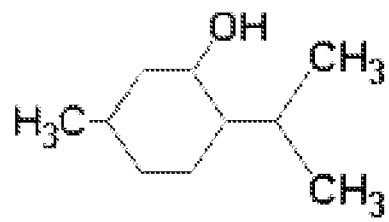
FIGS. 2A-2H depict the chemical structures of representative compatible additives.
Figure 2A:
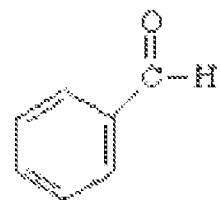
Figure 2A:
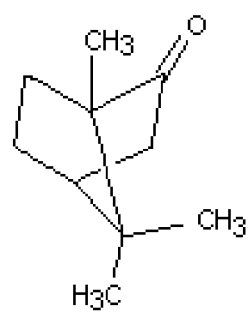
Figure 2B:
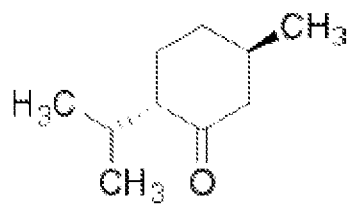
Figure 2B:
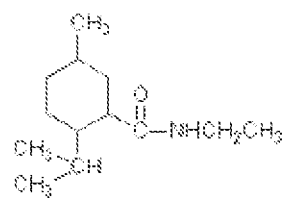
Figure 2B:
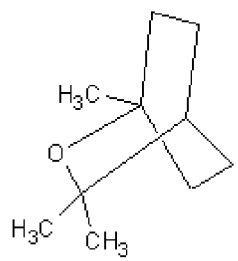
Figure 2C:
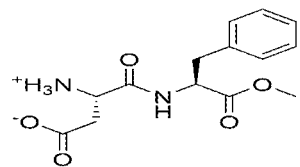
Figure 2C:
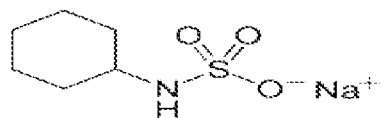
Figure 2C:
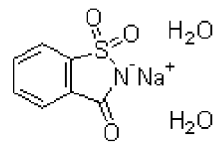
Figure 2D:
Figure 2D:
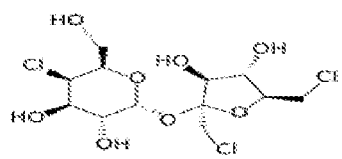
Figure 2D:
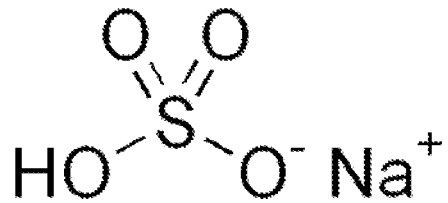
Figure 2E:
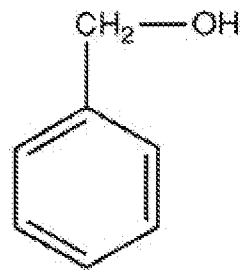
Figure 2E:
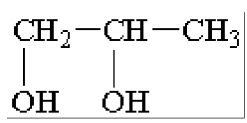
Figure 2E:
Figure 2F:
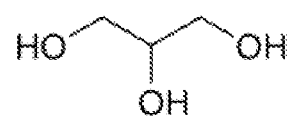
Figure 2F:
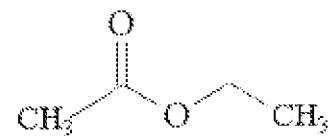
Figure 2F:
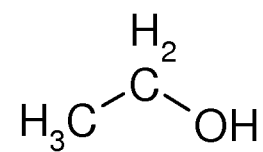
Figure 2G:
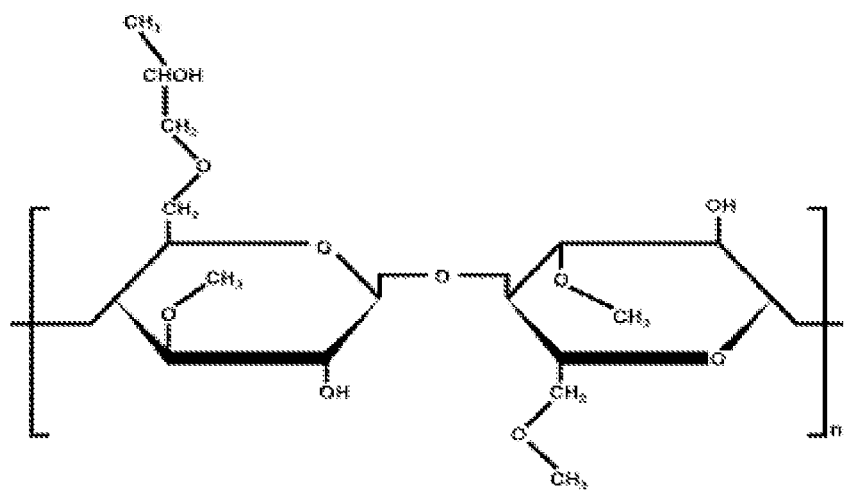
Figure 2G:
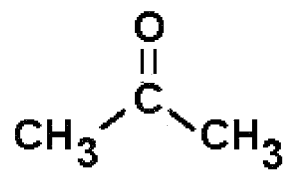
Figure 2G:
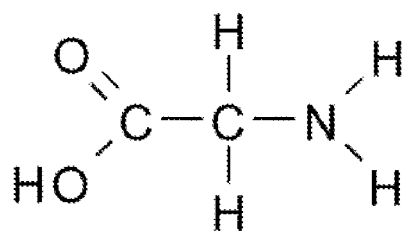
Figure 2H:
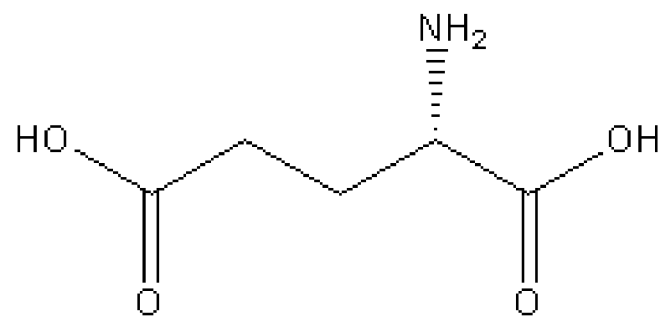
Figure 2H:
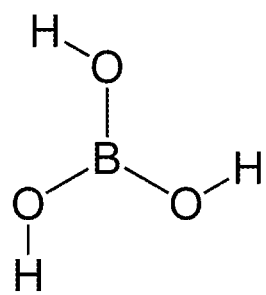
Figure 2H:
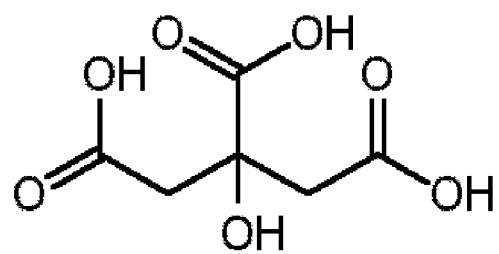
Figure 3A:
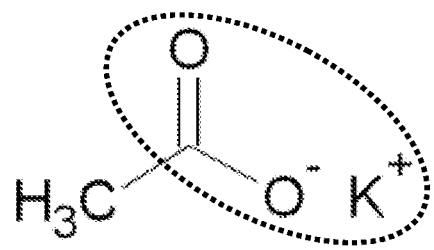
FIG. 3A-3F depicts the chemical structures of representative non-compatible additives.
Figure 3A:
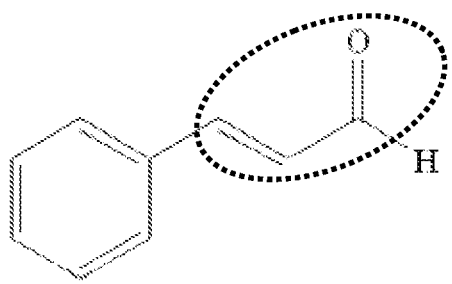
Figure 3A:
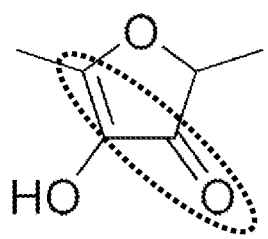
Figure 3B:
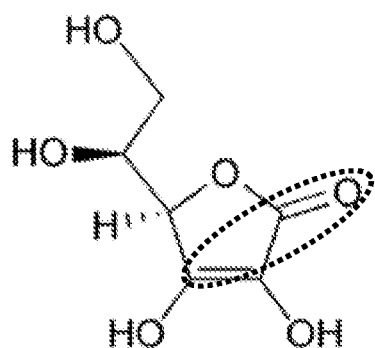
Figure 3B:
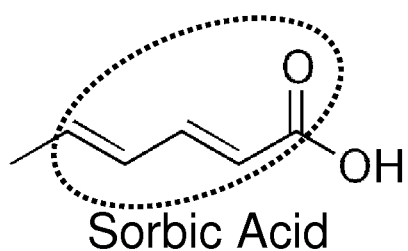
Figure 3B:
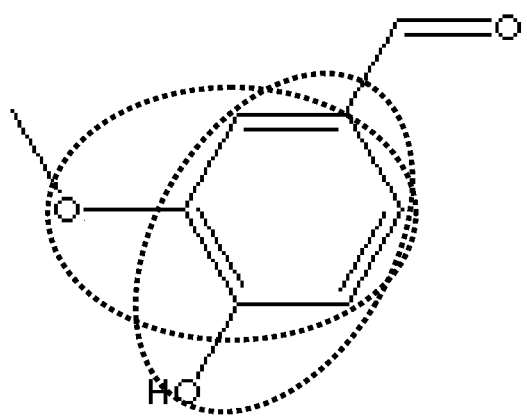
Figure 3C:
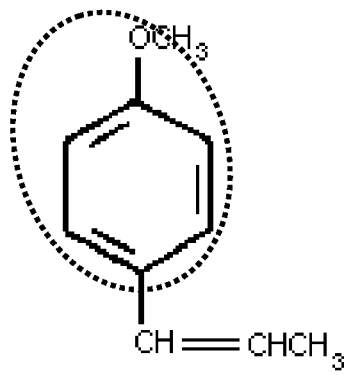
Figure 3C:
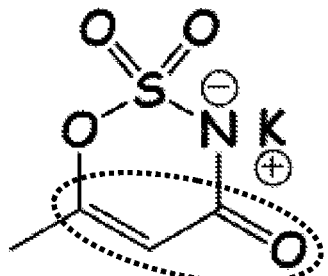
Figure 3C:
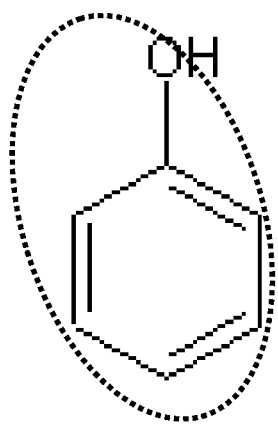
Figure 3D:
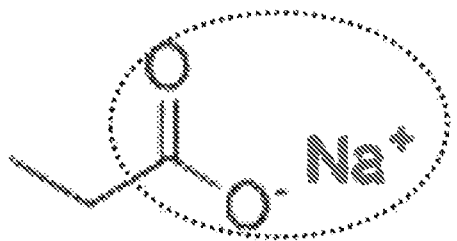
Figure 3D:
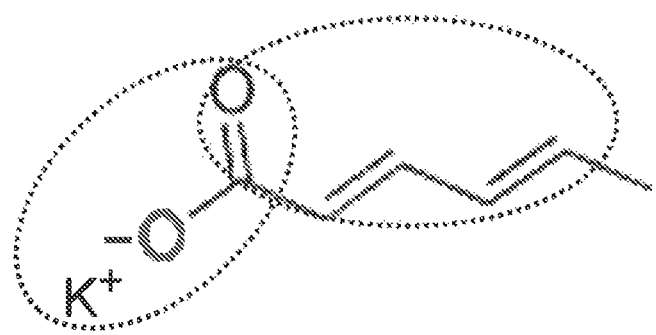
Figure 3E:
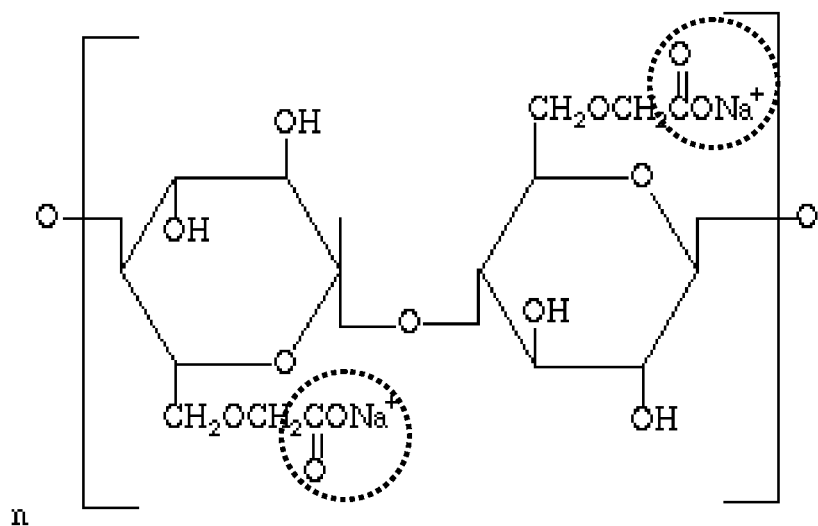
Figure 3E:
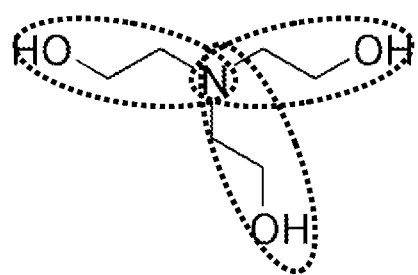
Figure 3F:
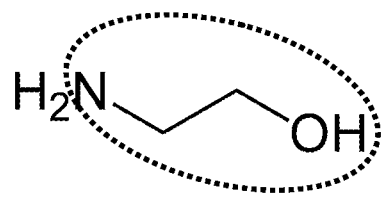
Figure 3F:
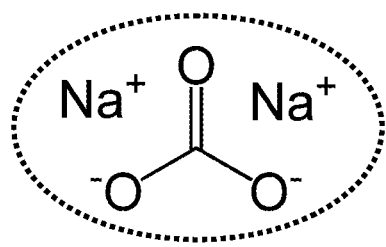

The disclosure describes a chlorine dioxide containing composition including at least one compatible additive. In some embodiments, the composition further comprises a non-compatible additive in a limited amount, as described below. Methods of making and using the composition are also provided.

DEFINITIONS

Unless defined otherwise, all technical and scientific terms used herein generally have the same meaning as commonly understood by one of ordinary skill in the art. Generally, the nomenclature used herein and the laboratory procedures in cytopathicity analysis, microbial analysis, organic and inorganic chemistry, and dental clinical research are those well known and commonly employed in the art.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent on the context in which it is used. Generally, "about" encompasses a range of values that are plus/minus 10% of a reference value. For instance, "about 25%" encompasses values from 22.5% to 27.5%.

It is understood that any and all whole or partial integers between any ranges set forth herein are included herein.

As used herein, "biocidal" refers to the property of inactivating or killing pathogens, such as bacteria, algae, viruses, and fungi (e.g., anti-bacterial, anti-algal, antiviral and antifungal).

As used herein, an "efficacious amount" of an agent is intended to mean any amount of the agent that will result in a desired biocidal effect, a desired cosmetic effect, and/or a desired therapeutic biological effect. In one example, an efficacious amount of an agent used for tooth whitening is an amount that will result in whitening of a tooth with one or more treatments.

The term "particulate" is defined to mean all solid materials. By way of a non-limiting example, particulates may be interspersed with each other to contact one another in some way. These solid materials include particles comprising big particles, small particles or a combination of both big and small particles.

As used herein, a "particulate precursor of chlorine dioxide" refers to an intimate mixture of chlorine dioxide-forming reactants that are particulate. An "intimate mixture" refers to a substantially homogenous mixture of the particulate reactants, wherein any one reactant particulate can possibly be contacting any other particulate reactant. Granules of ASEPTROL® and ENLUXTRA® (BASF, Florham Park, N.J.) are exemplary particulate precursors of chlorine dioxide.

As used herein the term "acid source" refers to a material, usually a particulate solid material, which is itself acidic or produces an acidic environment when in contact with liquid water or solid oxy-chlorine anion.

As used herein, the term "source of free halogen" or "free halogen source" means a compound or mixtures of compounds which release halogen upon reaction with water. As used herein, the term "free halogen" means halogen as released by a free halogen source.

As used herein, "substantially pure chlorine dioxide solution" refers to a solution of chlorine dioxide that has a non-cytotoxic concentration of oxy-chlorine anion. As used herein, "substantially pure chlorine dioxide solution" also refers to a concentrated solution of chlorine dioxide that contains a concentration of oxy-chlorine anion that, upon dilution to an efficacious amount of chlorine dioxide, is not cytotoxic with respect to the concentration of oxy-chlorine anion.

As used herein, "oxy-chlorine anion" refers to chlorite ($ClO_2^-$) and/or chlorate ($ClO_3^-$) anions.

As used herein, "cytotoxic" refers to the property of causing lethal damage to mammalian cell structure or function. A composition is deemed "substantially non-cytotoxic" or "not substantially cytotoxic" if the composition meets the United States Pharmacopeia (USP) biological reactivity limits of the Agar Diffusion Test of USP <87>"Biological Reactivity, in vitro," (approved protocol current in 2007) when the active pharmaceutical ingredient (API) is present in an efficacious amount.

As used herein, "irritating" refers to the property of causing a local inflammatory response, such as reddening, swelling, itching, burning, or blistering, by immediate, prolonged, or repeated contact. For example, inflammation of the gingival tissue in a mammal is an indication of irritation to that tissue. A composition is deemed "substantially non-irritating" or "not substantially irritating" if the composition is judged to be slightly or not irritating using any standard method for assessing dermal or mucosal irritation. Non-limiting examples of methods useful for assessing dermal irritation include the use of in vitro tests using tissue-engineered dermal tissue, such as EpiDerm™ (MatTek Corp., Ashland, Mass.), which is a human skin tissue model (see, for instance, Chatterjee et al., 2006, Toxicol. Letters 167: 85-94) or ex vivo dermis samples. Non-limiting examples of methods useful for mucosal irritation include: HET-CAM (hen's egg test-chorioallantoic membrane); slug mucosal irritation test; and in vitro tests using tissue-engineered oral mucosa or vaginal-ectocervical tissues. Other useful method of irritation measurement include in vivo methods, such as dermal irritation of rat or rabbit skin. See, for instance, the Draize skin test (OECD, 2002, Test Guidelines 404, Acute Dermal Irritation/Corrosion) and EPA Health Effects Testing Guidelines; OPPTS 870.2500 Acute Dermal Irritation. The skilled artisan is familiar with art-recognized methods of assessing dermal or mucosal irritation The term "stable," as used herein, is intended to mean that the components used to form chlorine dioxide, i.e., the chlorine dioxide-forming reactants, are not immediately reactive with each other to form chlorine dioxide. It will be understood that the components may be combined in any fashion, such as sequentially and/or simultaneously, so long as the combination is stable until such time that $ClO_2$ is to be generated.

The term "non-reactive," as used herein, is intended to mean that a component or ingredient as used is not immediately reactive to an unacceptable degree with other components or ingredients present to form chlorine dioxide or mitigate the ability of any component or ingredient to perform its function in the formulation at the time of use. As the skilled artisan will recognize, the acceptable timeframe for non-reactivity will depend upon a number of factors, including how the formulation is to be formulated and stored, how long it is to be stored, and how the formulation is to be used. Accordingly, the timeframe for "not immediately reactive" will range from one or more minutes to one or more hours to one or more weeks. In one embodiment, the timeframe is a range of minutes, for instance, from one minute to about 60 minutes. In another embodiment, the timeframe is a range of hours, for instance, from about one hour to about 24 hours. In yet another embodiment, the timeframe is a range of days, for instance, from about one day to about one week. In yet another embodiment, the timeframe is a range of weeks, for instance, from about one week to about 4-6 weeks.

As used herein, "hard tooth tissue" refers to at least one of enamel and dentin.

As used herein, "hard tooth tissue damage" refers to at least one of a reduction of microhardness of enamel, a reduction of microhardness of dentin, an increase in the surface roughness of enamel and an increase in the surface roughness of dentin.

As used herein, a composition "does not substantially damage hard tooth tissue" if one or more of the following is met for a tooth after treatment relative to the tooth prior to treatment: 1) enamel microhardness is decreased by an amount less than about 15% and/or the reduction is not statistically significant at the 5% confidence level; 2) dentin microhardness is decreased by an amount less than about 15% and/or the reduction is not statistically significant at the 5% confidence level; 3) enamel surface roughness is increased by an amount no more than about 20% and/or the increase is not statistically significant at the 5% confidence level; and 4) dentin surface roughness is increased by an amount no more than about 8% and/or the increase is not statistically significant at the 5% confidence level.

As used herein, "tooth whitening" refers to a lightening of tooth shade relative to the tooth shade prior to treatment. Lightening can be assessed on an isolated or an in situ tooth by standard, art-recognized methods of assessing tooth shade, which include qualitative, quantitative and semi-quantitative methods. For instance, lightening can be assessed by simple visual inspection, e.g., by comparing "before" and "after"

photographs of the treated teeth. Alternatively, a tooth can be deemed whitened when the tooth shade relative to the tooth shade prior to treatment is two or more shades lighter, as assessed by Vita classical shade guide (preferably under controlled visible light conditions) or two or more levels as assessed using the Vita Bleachedguide 3D-MASTER Shade system, which utilizes a multiple color spectrophotometer and includes half lightness levels. A difference of one shade is referred to herein as a "shade value unit" (SVU). Thus, for example, a difference of two shades is a 2 SVU difference.

As used herein, the phrase "oxidizing agent" refers to any material that attracts electrons, thereby oxidizing another atom or molecule and thereby undergoing reduction. Exemplary oxidizing agents include chlorine dioxide and peroxides, such as hydrogen peroxide.

As used herein, a "functional level" of an additive refers to any concentration at which the additive is typically used for its intended property or function in a composition, such as an oral care composition. The term can refer to a range of concentrations. The particular value or range of values of a functional level for an additive is related to the specific additive, the other components of the composition and the intended property or function for that additive in the composition. The "minimum functional level" for an additive refers to the lowest concentration at which the intended property or function is achieved for a given composition.

Unless otherwise indicated or evident from context, preferences indicated above and herein apply to the entirety of the embodiments discussed herein.

DESCRIPTION

Provided is a composition containing chlorine dioxide, a vehicle, and at least one compatible additive. In some embodiments, the composition optionally comprises a non-compatible additive in a compatible amount. As used herein, a compatible additive is a compound that is substantially non-reactive with chlorine dioxide. "Substantially non-reactive" means that at a functional level, the loss of chlorine dioxide in a sample initially containing 200 ppm chlorine dioxide does not exceed 13% eight (8) hours after preparation of the composition (excluding any initial rapid decline, e.g., steep decline within initial about 60 minutes after preparing a composition, due to impurities in an additive). In some embodiments, "substantially non-reactive" means the loss of chlorine dioxide does not exceed 10% at about 8 hours, excluding any initial rapid decline, e.g., steep decline within initial about 60 minutes after preparing a composition, due to impurities in an additive. Moieties that are found in compatible additives include, but are not limited to, saturated and cyclic hydrocarbons, aromatics, non-ionized non-aromatic carboxylic acids, amines, ethers, aldehydes, ketones, alcohols, and quaternary ammonium salts. Exemplary compatible additives include, but are not limited to, L-menthol, benzaldehyde, camphor, methone, ethyl menthane carboxamide, eucalyptol, aspartame, sodium cyclamate, sodium saccharin dihydrate, sucralose, cetylpyridinium chloride, benzoyl alcohol, propylene glycol, polyethylene glycol 400, glycerol, ethyl acetate, ethanol, hydroxypropyl methylcellulose, acetone, boric acid, sodium bisulfate, and non-ionized non-aromatic carboxylic acids such as glycine, 1-glutamic acid, and citric acid. The chemical structures of these representative compatible additives are depicted in FIGS. 2A-2H.

A compatible additive does not comprise any excluded functionalities. As used herein, excluded functionalities are: conjugated double bonds such as C=C—C=O, oxygen atoms adjacent to aromatic rings ("phenolic-type" oxygen, including ether oxygen), ionized salts of carboxylic acids, amino-ethanols (R1-N—$CH_2$—$CH_2$—OH) and inorganic carbonate salts ($XCO_3$). A non-compatible additive refers to a compound comprising one or more of the excluded functionalities. Additives containing such moieties include, but are not limited to, phenol, methyl salicylate, potassium acetate, t-cinnamaldehyde, cinnamic acid, furaneol, ascorbic acid, sorbic acid, methyl vanillin, anethole, acesulfame potassium, sodium propionate, potassium sorbate, sodium carboxymethylcellulose, triethanolamine, monoethanolamine, and sodium carbonate. The chemical structures of these exemplary non-compatible additives are depicted in FIGS. 3A-3F.

Non-compatible additives can be stratified into those which substantially completely consume the chlorine dioxide after 8 hours and those which consume less than about 45% of the chlorine dioxide after 8 hours. The latter type of non-compatible additive can be used in a composition in some embodiments, provided it is present in a compatible amount. A compatible amount of a non-compatible additive, as used herein, refers to a concentration of a non-compatible additive that is a functional level and at which no more than about 45% decrease in chlorine dioxide, about 30% decrease or about 15% decrease in chlorine dioxide occurs after 8 hours. In one embodiment, the non-compatible additive is selected from a flavor, a preservative and a thickener. In one embodiment, the thickener can be sodium carboxymethylcellulose (NaCMC).

A compatible additive can be identified by reviewing its chemical structure. A compatible additive does not comprise any of conjugated double bonds such as C=C—C=O, oxygen atoms adjacent to aromatic rings ("phenolic-type" oxygen, including ether oxygen), ionized salts of carboxylic acids, amino-ethanols (R1-N—$CH_2$—$CH_2$—OH) and inorganic carbonate salts ($XCO_3$). A compatible additive can comprise one or more of saturated and cyclic hydrocarbons, aromatics, non-ionized non-aromatic carboxylic acids, amines, ethers, aldehydes, ketones, alcohols, and quaternary ammonium salts.

Compatibility of an additive can be confirmed by either one of two methods: UV/Vis absorption or titration. Generally, the absorption method is used when an additive is soluble in water and produces a clear solution and is free of any dispersed phase. If absorption cannot be used, titration is used. In the absorption method, the absorption of a sample at 445 nm is determined and is converted to an amount of chlorine dioxide based on chlorine dioxide standards. UV/Vis spectrophotometers pre-calibrated to 445 nm by the manufacturer are commercially available from Hach Co. In the titration method, the concentration of chlorine dioxide in an aliquot is determined by reacting $ClO_2$ with an excess of potassium iodide at neutral pH to form iodine in aqueous solution. The iodine solution is then titrated with sodium thiosulfate solution using a starch indicator to a colorless endpoint. Kits for this titration method are available commercially from, for instance, Hach Co.

Compatibility is assessed using a composition comprising 200 ppm chlorine dioxide. While compatibility of an additive is assessed in a 200 ppm chlorine dioxide composition, the claimed compositions can have between about 0.5 to about 2000 ppm chlorine dioxide (and any integer value inbetween).

For water soluble additives, compatibility is measured in the substantial absence of other components. Thus, compatibility is assessed for a composition consisting of chlorine dioxide, water and the additive, and can include minute quantities of contaminants present in the additive and/or components derived from the chlorine dioxide-forming reactants.

For water-insoluble additives that are solid, a co-solvent can be used to obtain a more uniform and better dispersion of the insoluble solid additive. For instance, an insoluble solid can be solubilized in a co-solvent. The resultant solution is then added drop wise to water. As the solution mixes with the water, the additive solids precipitate as a fine dispersion. Exemplary co-solvents include compatible carriers such as propylene glycol, polyethylene glycol 400, glycerol, ethyl acetate and ethanol. For water-insoluble liquids, such as oils, the oil can be added to water with sufficient agitation to create fine droplets; the fine droplets facilitate mass transfer between the oil and water phases.

There are typical ranges for additives which generally encompass the ranges at which the additive is present at a functional level. Typical concentration ranges for categories of currently-known additives that are commonly used in oral care compositions can be as follows. A sweetener is typically used at about 0.5 wt. % to about 1.0 wt. %. A flavor agent is typically used at about 0.4 wt. % to about 1.1 wt. %. An antiseptic is typically used at about 0.1 wt. % to about 0.5 wt. %. A preservative is typically used at about 0.1 wt. % to about 0.5 wt. %. A carrier is typically used at about 0.8 wt. % to about 1.2 wt. %. A thickener is typically used at about 0.4 wt. % to about 2 wt. %. For other currently-known additives, typical concentrations can be: a pigment, about 1 to about 25 wt. %; a fragrance, about 0.1 to about 10 wt. %; a plasticizer, about 0.1 to about 20 wt. %; an encapsulate, about 0.1 to about 50 wt. %; an antitartar agent, about 0.01 to about 2 wt. %; an anticorrosion agent, about 0.01 to about 5 wt. %; a UV absorber, about 0.1 to about 50 wt. %; a cleaning agent, about 0.01 to about 80 wt. %; a buffer, about 1 ppm to about 5 wt. %; and an oxidizing agent (other than chlorine dioxide), at about 0.0001 to about 36 wt. %. These ranges are typical use ranges for existing additives but are not intended to be limiting. In addition, these teachings are not intended to exclude any future additive whose functional level is outside of these recited ranges.

In addition to chlorine dioxide and at least one compatible additive, the provided composition contains a vehicle. As used herein, a vehicle refers to any aqueous solution containing no ingredients that have an excluded functionality. Exemplary vehicles include, but are not limited to, water, mixtures of water and one or more compatible carriers such as propylene glycol, polyethylene glycol 400, glycerol, ethyl acetate and ethanol, and aqueous buffers. In an embodiment of the composition, the vehicle is water. In another embodiment, the vehicle is a mixture of water and propylene glycol.

In some embodiments, the composition disclosed herein comprises two, three or more compatible additives. As demonstrated herein, the decrease in chlorine dioxide due to a given additive appears to be largely cumulative. Therefore, addition of too many compatible additives and/or at too high a concentration can result in excessive decrease in chlorine dioxide. An excessive decrease in chlorine dioxide reduces the efficacy of the composition with respect to the function of the chlorine dioxide. In addition, it may result in production of non-desirable by-products, such as oxy-chlorine anion, which is known to cause cytotoxicity when present above certain levels. See commonly-assigned U.S. patent application Ser. Nos. 12/502,326 and 12/502,356, filed Jul. 14, 2009, entitled "Non-Cytotoxic Chlorine Dioxide Fluids." Consideration of the absolute quantity of chlorine dioxide decrease in the composition is prudent due to such non-desirable by-products. Accordingly, in some embodiments, the reduction of chlorine dioxide is no more than about 200 ppm, no more than about 100 ppm, or no more than about 50 ppm. In these embodiments, the % total decrease in chlorine dioxide is therefore directly related to the initial amount of chlorine dioxide present. For instance, in a composition comprising 500 ppm chlorine dioxide, where the total reduction of chlorine dioxide is no more than 100 ppm, the % total decrease in chlorine dioxide is therefore no more than about 20% after 8 hours. In a composition comprising about 200 ppm chlorine dioxide, where the total reduction of chlorine dioxide is no more than 100 ppm, the % total decrease is therefore no more than about 50% after 8 hours.

Exemplary compatible additives used as sweeteners include, but are not limited to: aspartame, sodium cyclamate, sodium saccharin dihydrate, and sucralose. Exemplary compatible flavor additives include, but are not limited to: L-menthol, benzaldehyde, camphor, menthone, methyl menthane carboxamide, and eucalyptol. Exemplary compatible additives used as preservatives include, but are not limited to, benzyl alcohol. Cetylpyridinium chloride is an example of a compatible additive used as an antiseptic. Hydroxypropyl methylcellulose is an example of a compatible thickener additive. Exemplary buffers include, but are not limited to, glycine, 1-glutamic acid, boric acid, citric acid and sodium bisulfate.

Based on the data herein, it is expected that the following additives are compatible additives: isoamyl acetate and limonene (fragrances); polyisobutylene and methylcellulose (encapsulates); sodium lauryl sulfate and cetyltrimethylammonium chloride (surfactants); diisobutyl phthalate (plasticizer); citric acid and acetic acid (scale removers); dimethyl methylphosphonate (scale inhibitor); and dicyclohexylamine (corrosion inhibitor). Propionic acid and acetic acid are also expected to be compatible additives, based on the data herein.

The amount of chlorine dioxide in a composition relates to the intended use of the composition. The skilled artisan can readily determine the appropriate amount or amount range of chlorine dioxide to be efficacious for a given use. Generally, chlorine dioxide containing compositions described herein comprise between at least about 0.5 parts-per-million (ppm) chlorine dioxide to about 2000 ppm. In some embodiments, the chlorine dioxide concentration ranges from about 5 to about 700 ppm, from about 20 to about 500 ppm, and from about 30 to about 200 ppm chlorine dioxide. Lower concentrations in the range of about 0.5 to about 500 ppm are useful when used in the mouth or near the nose so as to minimize exposure to the possible chlorine-like odor of a chlorine dioxide-containing composition. Higher concentrations in the range of about 20 to about 2000 ppm are useful when used in areas containing a substantial concentration of reactive organic material, such as wound fluid in wounds or for hard surface treatments. Higher concentrations can also be advantageous to accelerate efficacy when treating relatively inert materials, such as dentures, outside of the oral cavity.

In some embodiments, such as compositions for oral care applications, the claimed composition can be non-irritating, non-cytotoxic and/or can substantially not damage hard tooth tissue.

Oxidizing agents, such as peroxide, can be cytotoxic, even in very low amounts. Advantageously, chlorine dioxide can be a substantially non-cytotoxic oxidizing agent. Specifically, cytotoxicity in compositions comprising chlorine dioxide can arise from the presence of oxy-chlorine anions. Accordingly, a composition comprising chlorine dioxide that comprises zero milligram (mg) oxy-chlorine anion per gram composition to no more than about 0.25 mg oxy-chlorine anion per gram composition, preferably zero to about 0.24, 0.23, 0.22, 0.21, or 0.20 mg oxy-chlorine anion per gram composition, more preferably zero to about 0.19, 0.18, 0.17, 0.16, 0.15, 0.14, 0.13, 0.12, 0.11, or 0.10 mg oxy-chlorine anion per gram composition and more preferably still from zero to about 0.09, 0.08, 0.07, 0.06, 0.05 or 0.04 mg oxy-chlorine anion per gram composition, absent other components (e.g., additives and/or vehicle) that contribute to cytotoxicity, is substantially non-cytotoxic. In compositions wherein one or more other components cause cytotoxicity, the use of an efficacious amount of a non-cytotoxic oxidizing agent, such as chlorine dioxide, is advantageous in not substantially contributing to cytotoxicity.

Oxy-chlorine anions can be measured in these solutions using any method known to those skilled in the art, including ion chromatography following the general procedures of EPA test method 300 (Pfaff, 1993, "Method 300.0 Determination of Inorganic Anions by Ion Chromatography," Rev. 2.1, US Environmental Protection Agency) or a titration method based on an amperometric method (Amperometric Method II in Eaton et al, ed., "Standard Methods for the Examination of Water and Wastewater" 19th edition, American Public Health Association, Washington D.C., 1995). Alternatively, oxy-chlorine anions may be measured by a titration technique equivalent to the amperometric method, but which uses the oxidation of iodide to iodine and subsequent titration with sodium thiosulfate to a starch endpoint in place of the amperometric titration. A chlorite analytical standard can be prepared from technical grade solid sodium chlorite, which is generally assumed to comprise about 80% by weight of pure sodium chlorite.

While a preferred chlorine dioxide composition is low in oxy-chlorine anion concentration, depending upon how it is produced it may contain ions of other types (such as sodium and magnesium cations and sulfate and chloride anions). The ionic concentration of an ionic solution may be expressed as its ionic strength, which is defined as:

$$\text{Ionic Strength} = \tfrac{1}{2}\Sigma c_i z_i^2 \quad (1)$$

where $c_i$ is the concentration of ion "i" (in moles/liter) and $z_i$ is the charge of ion "i". This product is summed over all the ions in the solution.

The stability of a chlorine dioxide composition should be measured in solution at an ionic strength similar to that in which the chlorine dioxide will be utilized. Common ionic strengths (in moles/liter) range from zero for pure chlorine dioxide solution to slightly above zero to over a thousand moles per liter for chlorine dioxide in salt water (such as isotonic oral rinse solution). Specifically, the ionic strength of the chlorine dioxide composition can be zero (0), or about 5%, or about 10%, or about 20%, or about 40%, or about 60%, or about 80%, or about 100%, or about 150%, or about 200%, or about 5 times, or about 10 times, or about 100 times, or about 1000 times, or more of the concentration of chlorine dioxide in the composition (in moles/liter). For example, a composition comprising 10 ppm (i.e., 10 mg/liter) of chlorine dioxide in isotonic saline (0.9% by weight NaCl) solution will have an ionic strength that is about 1050 times its concentration of chlorine dioxide (0.9% NaCl solution=0.155 moles/liter, 10 mg/liter $ClO_2$=0.000148 moles/liter, 0.155/0.000148=1047). In an embodiment, the ionic strength of the composition described herein is at least about 5%, at least about 10% or at least about 20% of the concentration of chlorine dioxide in the composition (in moles/liter).

Soft tissue irritation can result from highly reactive oxygen species, such as those found in peroxide based compositions. Soft tissue irritation can also result from extremes of pH, both acidic and basic. Advantageously, the claimed composition minimizes soft tissue irritation by not including highly reactive oxygen species and by moderating the pH. To minimize soft tissue irritation of the chlorine dioxide containing composition, the composition has a pH of at least about 2.5. To minimize possible hard surface erosion, the composition has a pH of at least about 4.5. In some embodiments, the composition has a pH of at least about 5, or greater than about 6. In certain embodiments, the pH ranges from about 4.5 to about 11, from about 5 to about 9, or greater than about 6 and less than about 8. In one embodiment, the pH can be about 6.5 to about 7.5.

The claimed composition can be made by any method known in the art. Exemplary methods are disclosed in commonly-assigned U.S. patent application Ser. Nos. 12/502,326 and 12/502,356, filed Jul. 14, 2009. In some embodiments, a composition can be prepared by combining a substantially pure chlorine dioxide solution with one or more compatible additives, a vehicle and optionally a compatible amount of a non-compatible additive. In preparing a composition of the disclosure, one or more components of the composition can be combined prior to the time of preparation of the composition. For instance, for an additive that is not soluble in water, the additive can be first combined with a compatible carrier. The resultant mixture can be then combined with a vehicle, chlorine dioxide and any other compatible additives. Alternatively, all components of a composition can be prepared at the time of use. In most embodiments, the substantially pure chlorine dioxide solution is generally prepared immediately before its combination with a compatible additive and any additional vehicle. In embodiments including a compatible amount of a non-compatible additive, the non-compatible additive can be added to the composition last. The vehicle in the final prepared composition can be a combination of vehicles from precursor solutions. For instance, in a composition prepared from a concentrated buffered solution of chlorine dioxide, an additive/carrier solution and water, the final vehicle can be formed by the buffered solution, the carrier and the water. Other combinations will be readily apparent to the skilled artisan.

Substantially pure chlorine dioxide can be prepared by preparing chlorine dioxide by any known method, then bubbling a gas (e.g., air) through that solution (sparging) and into a second container of deionized water, to prepare the product solution of substantially pure chlorine dioxide. Only $ClO_2$ and possibly some water vapor is transferred from the source solution to the product solution. All the salt ingredients and acid remain behind in the source solution. Thus, there are no oxy-chlorine anions in the substantially pure product solution. One method of preparing chlorine dioxide comprises combining an aqueous solution of sodium chlorite with a mineral acid to reduce the solution pH to below about 3.5 and allowing the solution to react for a sufficient time, e.g., about 30 minutes, to generate chlorine dioxide. The resulting solution is then sparged as described above to prepare the product solution of substantially pure chlorine dioxide.

Substantially pure chlorine dioxide can also be prepared using a pervaporation technique, such as that disclosed in U.S. Pat. No. 4,683,039. In addition, a metal chlorite and an acid source can be reacted in solution to yield high conversion to chlorine dioxide and produce a greater than 2000 ppm chlorine dioxide solution. The concentrated solution can then be buffered to a neutral pH. Similarly, a chlorine dioxide solution can be prepared using the composition described in U.S. Pat. No. 5,399,288, which yields a high concentration chlorine dioxide solution at acidic pH. The concentrated solution can then be buffered to achieve a substantially neutral pH to prepare a substantially pure chlorine dioxide solution.

Another source of a substantially pure chlorine dioxide solution is chlorine dioxide is prepared using an ASEP-TROL® (BASF Corp., Florham Park, N.J.) material, which are described in commonly-assigned U.S. Pat. Nos. 6,432,322 and 6,699,404. These patents disclose substantially anhydrous solid bodies comprising particulate reagents for preparing highly-converted solutions of chlorine dioxide when added to water. The particulate reagents in the solid bodies comprise a metal chlorite such as sodium chlorite, an acid source such as sodium bisulfate and optionally a source of free halogen such as the sodium salt of dichloroisocyanuric acid or a hydrate thereof (collectively referred to herein as "NaDCCA"). Chlorine dioxide is generated when an ASEPTROL® material is contacted with water or an aqueous medium. ASEPTROL® material can be made to have an extremely high conversion rate in an aqueous solution, as described in U.S. Pat. Nos. 6,432,322 and 6,699,404, resulting in high concentrations of chlorine dioxide and low concentrations of oxy-chlorine anion. Thus, ASEPTROL® materials provide a way to efficiently generate chlorine dioxide at substantially neutral pH, thus avoiding problems existing with earlier, acidic chlorine dioxide-based products.

Chlorites useful in preparing chlorine dioxide include metal chlorites. The metal chlorite can generally be any metal chlorite. In some embodiments, the metal chlorite can be an alkali metal chlorite, such as sodium chlorite and potassium chlorite. Alkaline earth metal chlorites can also be employed. Examples of alkaline earth metal chlorites include barium chlorite, calcium chlorite, and magnesium chlorite. In many embodiments, the metal chlorite is sodium chlorite.

The acid source can include inorganic acid salts, salts comprising the anions of strong acids and cations of weak bases, acids that can liberate protons into solution when contacted with water, organic acids, and mixtures thereof. In another aspect, the acid source can be a particulate solid material that does not react substantially with the metal chlorite during dry storage, however, does react with the metal chlorite to form chlorine dioxide when in the presence of the aqueous medium. The acid source may be water soluble, substantially insoluble in water, or intermediate between the two. Exemplary acid sources are those that produce a pH of below about 7, and below about 5.

Exemplary substantially water-soluble, acid-source-forming components include, but are not limited to, water-soluble solid acids such as boric acid, citric acid, tartaric acid, water soluble organic acid anhydrides such as maleic anhydride, and water soluble acid salts such as calcium chloride, magnesium chloride, magnesium nitrate, lithium chloride, magnesium sulfate, aluminum sulfate, sodium acid sulfate ($NaHSO_4$), sodium dihydrogen phosphate ($NaH_2PO_4$), potassium acid sulfate ($KHSO_4$), potassium dihydrogen phosphate ($KH_2PO_4$), and mixtures thereof. In some embodiments, the acid-source-forming component can be sodium acid sulfate (sodium bisulfate). Additional water-soluble, acid-source-forming components are known to those skilled in the art.

Further provided is a precursor composition useful for preparing the compositions described herein. The precursor composition comprises a mixture containing particulate chlorine dioxide-forming reactants (a metal chlorite, an acid source, and an optional halogen source), at least one compatible additive and optionally a compatible amount of a non-compatible additive. Such a precursor composition can be prepared so as to be non-reactive, thus forming a stable composition. Precursor compositions are generally protected from water and/or water vapor exposure and UV light exposure to avoid degradation of the components or premature reaction of the particulate chlorine dioxide-forming reactants. To prepare the composition, a vehicle is added to the precursor composition such that the generation of chlorine dioxide from the particulate chlorine dioxide-forming reactants is initiated.

The described composition can be used in any application that would benefit from the properties of a chlorine dioxide-containing composition. Properties of the chlorine dioxide composition include potent biocidal activity, deodorizing activity, and bleaching activity. Applications making use of such properties applications include, but are not limited to, oral care such as tooth whitening, mouthwash, and caries abatement, periodontal disease treatment, hand rinse, denture or toothbrush cleaning, hard surface cleansing, vaginal lavage, enema, wound treatment, skin care and treatment, burned skin treatment, skin bleaching, hair bleaching, odor abatement, fungal infections of toenail, nail, and/or skin, treatment of skin and mucosa Candida infection, and contact lens disinfection.

Accordingly, in one embodiment, a method of whitening a tooth is provided. The method comprises contacting a tooth surface with an efficacious amount of a composition containing chlorine dioxide, a vehicle, at least one compatible additive and optionally a non-compatible additive in a compatible amount. In some embodiments, the composition comprises chlorine dioxide, water, propylene glycol, one of sodium carboxymethylcellulose and HPMC, a flavorant selected from the group consisting of menthol, benzaldehyde, camphor, methone, ethyl menthane carboxamide, eucalyptolm and combinations thereof, and a sweetener selected from the group consisting of sucralose, aspartame, sodium cyclamate, sodium saccharin dihydrate, and combinations thereof. In some embodiments, the flavorant is menthol. In some embodiments, the sweetener is sucralose. The chlorine dioxide concentration can be from about 5 to about 500 ppm, about 20 to about 400 ppm, or about 40 to about 200 ppm. In some embodiments, the contacted tooth surface can be whitened by at least about 3 shade value units, at least about 5 shade value units, or at least about 6 shade value units. In some embodiments, the composition used in the method of whitening is non-irritating, non-cytotoxic and/or does not adversely affect enamel or dentin microhardness to a statistically significant extent. In some embodiments, the contacting step is iterated at least once, and optionally, more than once, in order to produce the desired degree of whitening, such as whitening the contacted tooth surface by at least a 3 shade value units. In one embodiment, the iterations are substantially contiguous. In another embodiment, the iterations are separated by a period of time, such as at least about 12 hours. The period of time can be longer as described elsewhere herein. In some embodiments, the composition does not substantially increase surface roughness of teeth, even after extended contact with the composition. Thus, tooth whitening can be obtained without substantially damaging hard tooth tissue. In some embodiments, microhardness of enamel contacted by a substantially non-cytotoxic composition is decreased less than about 15%, or less than about 10%, relative to the enamel prior to contact. In some embodiments, microhardness of dentin contacted by a substantially non-cytotoxic composition is decreased less than about 15%, or less than about 10%, relative to the enamel prior to contact. It is believed therefore that tooth whitening in accordance with the disclosed method can have reduced or substantially reduced tooth sensitivity and soft tissue irritation, compared to peroxide-based tooth whitening products currently available. It is further contemplated that the extent and/or rate of color rebound will be reduced, compared to peroxide-based tooth whitening products currently available.

The absence of soft tissue irritation advantageously permits the dental professional to proceed without a gum-protection step. Furthermore, substantial contact with soft oral tissue can be possible with compositions disclosed herein without irritation and/or cytotoxicity. "Substantial contact with soft oral tissue" as used herein refers to contact that is more than contact with gum tissue proximal to a treated tooth. Thus, substantial contact includes, but is not limited to, contact with gum, cheek mucosal and tongue tissue. Enamel and dentin surface roughness are also not substantially increased by contact with a composition of the disclosure. In some embodiments, surface roughness is increased by no more than about 20% or no more preferably than about 15% relative to the surface roughness prior to contact.

The duration of contact with the tooth to achieve a measurable degree of tooth whitening can be readily determined by the skilled artisan in view of the teachings herein. Advantageously, even after prolonged contact, the composition does not substantially damage hard tooth tissue. Generally, duration of contact ranges from seconds to minutes. In some embodiments, the duration of contact can be at least about 60 seconds, at least about 1, 2, 3, 4, or 5 minutes, at least about 6, 7, 8, 9, or 10 minutes, or at least about 11, 12, 13, 14, or 15 minutes. In some embodiments, contact duration can range up to 16, 17, 18, 19, or 20 minutes, further up to 21, 22, 23, 24, 25, 26, 27, 28, 29, or 30 minutes, and further up to about 35, 40, 45, 50, 55, or 60 minutes or longer in some circumstances. In certain embodiments, duration of contact ranges between about 1 and about 60 minutes, from about 5 minutes to about 30 minutes, or from about 10 to about 20 minutes. In some embodiments, duration of contact for a treatment is about 15 minutes. Treatment frequency is also readily determined by skilled artisan armed with the present disclosure. Treatment may comprise one episode of tooth contact or more than one episode. Treatment episodes may be contiguous, separated in time (e.g., a few hours to a few days, a few days to a few weeks, and also longer intervals including several months to a year or more) or both. In some embodiments, treatment comprises at least two substantially contiguous episodes of tooth contact. The contiguous episodes can be the same duration in time such as about 15 minutes or different durations of time such as 10 minutes and 20 minutes. In some embodiments, the composition for each episode is freshly made. As used herein, "freshly made" means that the addition of chlorine dioxide to the other components of the final composition, or the addition of the at least one additive and optional non-compatible additive to the chlorine dioxide component of the final composition, occurs within about one hour, within about 30 minutes, or within about 15 minutes before contacting a tooth surface with the composition.

Contact between the composition and the tooth surface can be achieved by any of a number of well-known methods in the art, as described in commonly-assigned U.S. application Ser. Nos. 12/502,761 and 12/502,781, filed Jul. 14, 2009 and entitled "Tooth Whitening Compositions and Methods." For instance, the composition can be brushed or spread onto the tooth surface, used as an oral rinse, present on a flexible strip or patch that can be pressed against and molded to the tooth surface, or can be placed in a dental tray that is then positioned on the teeth. Exemplary systems for preparing chlorine dioxide compositions are also disclosed in U.S. application Ser. Nos. 12/502,761 and 12/502,781.

The compositions and methods are further described in detail by reference to the following experimental examples. These examples are provided for purposes of illustration only, and are not intended to be limiting unless otherwise specified. Thus, the compositions and methods should in no way be construed as being limited to the following examples, but rather, should be construed to encompass any and all variations which become evident as a result of the teaching provided herein.

EXAMPLES

The chlorine dioxide reactivity of various additives commonly used in oral care compositions was assessed to determine if general rules could be identified regarding functional moieties and reactivity. Materials and methods are described first.

Sample Preparation:

Additives tested in this study included flavor blends, individual flavor ingredients (i.e., a single component of a flavor blend), non-caloric sweeteners, antimicrobial/antiseptic agents, and thickening agents. In addition, additives used as carriers or as preservatives were also tested. Chemicals not normally used as oral care additives were tested as model compounds to better understand the effect of a particular functional group.

Each additive was formulated with a 200 ppm $ClO_2$ stock solution to prepare a test sample; the concentration of the additive was consistent with typical use levels for an oral care product. For instance, in oral care products such as toothpaste and mouthwash, flavor blends are typically used at about 1 wt. %, sweeteners at about 0.5 wt. %, antimicrobial agents at about 0.1 wt. %, and thickeners at about 3 wt. %.

Test samples were prepared by weighing all of the raw materials on an analytical balance. After achieving a uniform mixture of the additive in water, a concentrated $ClO_2$ solution was added to achieve 200 ppm $ClO_2$ in the final resulting test sample. The date and time that the $ClO_2$ stock solution was added to the uniform mixture of the additive in water was documented. The compositions of the various test samples recorded in Tables 2 and 3 were calculated from the masses recorded during raw material weighing.

The ionic strength of a 200 ppm $ClO_2$ solution made using ASEPTROL® STab-10 as described, and absent addition of any other ions, is about 0.05 moles/liter.

The concentrated $ClO_2$ solution was prepared fresh daily using 1.5 gram tablets of the ASEPTROL® STab-10 formulation reacted with 0.75 liters of de-ionized water in a volumetric flask. The tablet is allowed to react 10 minutes before any agitation is applied to the solution. During this period, chlorine dioxide evolves from the tablet turning the solution yellow in color. After 10 minutes, all of the chlorine dioxide has been generated from the tablet and any undissolved portion of the tablet is incorporated into solution by inverting the volumetric flask several times. The actual concentration of $ClO_2$ is determined by sampling 10 ml and testing using the UV-visible absorption method. At least one control sample was made for every batch of $ClO_2$ stock solution that was made and was prepared using the same method and containers that were used to prepare the samples containing an additive.

For water-insoluble solid additives, it was advantageous to use an additional component to achieve a better, more uniform dispersion of the insoluble solid. A co-solvent that is not reactive with chlorine dioxide was used to dissolve the solid additive prior to the addition of the concentrated $ClO_2$ solution. For example, L-menthol crystals are insoluble in water. To prepare Comp. 1, the L-menthol crystals were dissolved in propylene glycol at 50 wt. %, and the resultant 50:50 menthol-propylene glycol solution was added drop wise into water to prepare a test sample having 0.511 wt. % L-menthol. As the propylene glycol solution mixed with the water, the menthol solids precipitated as a fine dispersion.

For water-insoluble oils (e.g., flavor oils), the oil was dispersed in water using sufficient agitation speeds to provide small droplets of oil to enhance mass transfer between the oil and water phases.

Analytic Tests:

Chlorine dioxide in each test sample was assessed by one of two methods: UV/Vis absorption or pH 7/potassium iodide/sodium thiosulfate titration.

I. General testing regimen: Each test sample was tested for chlorine dioxide at a minimum of three time points: immediately after mixing, at about 6 hours, and at about 24 hours after mixing the chlorine dioxide solution. In some cases, measurements at additional time points were taken as well. If the chlorine dioxide was found to be completely reacted at an early time point, testing of aliquots at later time points was not performed.

II. Absorption Method: If a test sample was clear and free of any dispersed phase (e.g., oil droplets, cloudiness, precipitate, etc), the chlorine dioxide concentration was measured at 445 nm using the "75 Chlor Method" on the Hach DR2400 Portable Spectrometer (Hach Co., Loveland, Colo.). The instrument manufacturer calibrates the absorption of the spectrometer at 445 nm with chlorine dioxide standards. The method (Hach DR/2400, Chlorine Dioxide Method 8138, Direct Reading Method, 2002) is carried out in accordance with the user manual for the DR2400 portable spectrometer.

III. Titration: If a test sample could not be measured by the UV/Vis absorption method due to turbidity from a dispersed phase, the concentration of chlorine dioxide in aliquots of the test sample was determined by reacting $ClO_2$ with an excess of potassium iodide at neutral pH to form iodine in aqueous solution. The iodine solution was then titrated with sodium thiosulfate solution using a starch indicator to a colorless endpoint. The titration was performed using a Hach digital titrator device (Hach Co., Catalog #1690001). In brief, a volume of pH 7 phosphate buffer solution is added to the solution to be tested, to which potassium iodide (KI) crystals are then added. The resulting solution is titrated with a sodium thiosulfate solution until the test solution turns a light straw color. A few drops of the starch indicator solution is added, turning the solution blue. The solution is then titrated to a colorless endpoint and the volume of titrant (Titer7) noted. Calculation of the chlorine dioxide concentration, assuming that no chlorine or other reactive oxidizers are present, is:

$$[ClO_2] = \frac{N \times Titer7 \times M}{V} \quad (2)$$

$[ClO_2]$=Concentration of $ClO_2$ in solution, mg/liter
N=Normality of sodium thiosulfate solution, equivalents/liter
Titer7=Volume of sodium thiosulfate solution to reach colorless endpoint, ml
M=is the molar weight of $ClO_2$ in mg per mole
V=Volume of the aliquot, ml Containers:

To minimize the loss of chlorine dioxide from test samples having water-like viscosity, the test samples were prepared in 8-oz brown glass jars with enough material to completely fill the jar and thereby eliminate the gaseous head space. Brown glass prevents exposure of the samples to UV light; UV light can degrade chlorine dioxide. Solutions were continuously stirred with a magnetic stirrer and a TEFLON-coated (DuPont, Wilmington, Del.) magnetic stir bar. For the titration method of assessing chlorine dioxide, each jar was opened at several time points, and an aliquot removed for testing. As a result, some volatile chlorine dioxide gas might be lost from the container during the sampling process. The date and time that an aliquot was transferred from the jar for analysis was recorded.

For test samples that were analyzed by UV/Visible spectroscopy, the test sample was prepared in a standard 10 mL Hach glass vial. An advantage of the absorption method is that the sample is never consumed as part of the analytical method. Therefore, the initial sample in the Hach vial never needed to be open after the solutions were prepared, eliminating any possibility of $ClO_2$ being lost from repeated opening and closing of the container. Since the Hach vials are clear, the vials were stored in the dark between measurements to minimize exposure to UV light.

For the titration method of high viscosity fluids, headspace was eliminated by preparing the high viscosity sample solutions in syringes. This method of preparation is only feasible if the dispersed mixtures do not separate readily into two or more phases. An example of a dispersed mixture that does not readily separate is a viscous polymeric solution that contains air bubbles or an insoluble flavor ingredient like menthol crystals. A large volume syringe (approximately 20-ml or larger) or multiple syringes of the same sample were needed to provide a sufficiently large sample (about 5 grams per titration) for multiple titrations. The syringe technique allowed the sample to be dispensed directly into the solution containing the reagents that sequester any chlorine dioxide as part of the titration method. Dispensing samples directly from the syringes into the sequestering solutions reduces the loss of chlorine dioxide that is typically experienced during the transfer of an aliquot from jars to the titration solution.

Data Analysis:

Chlorine dioxide concentration was plotted as a function of time, where time zero corresponds to the contact of the concentrated $ClO_2$ stock solution with the aqueous mixture of the ingredient under test. To compare the reactivity of $ClO_2$ with the various additives tested, the decrease of $ClO_2$ at 8 hours of exposure to the additive was estimated by interpolation for each ingredient. The interpolation was done for 8 hours, since this is a reasonable use-life for a chlorine dioxide containing composition, such as whitening product used in a dental professional's office. The percentage decrease was determined using the following equation:

$$\% \text{ Decrease@8 Hours} = (1 - [ClO_2]_{t=8 \text{ hours}} \div [ClO_2]_{t=initial}) * 100\% \quad (3)$$

For most additives, the percent decrease was calculated using the concentration measured immediately after mixing. For a few additives, the initial value was 0 ppm or very, very low; therefore, the concentration of the control solution at time zero had to be used to calculate the percent decrease.

The results are presented below.

FIG. 1A depicts the concentration versus time data for chlorine dioxide reacting with five individual sweeteners: aspartame, sodium cyclamate, sodium saccharin dihydrate, sucralose, and acesulfame potassium. Aspartame, sodium cyclamate, sodium saccharin dihydrate, and sucralose each show steep immediate declines in chlorine dioxide concentration, followed by much more gradual declines. While not wishing to be bound by theory, it is believed that the initial steep decline (within about the first 60 minutes) is due to one or more impurities in the additives, which react rapidly with chlorine dioxide. After the impurities are consumed, the resulting $ClO_2$ decrease is believed attributably largely to the additive's reaction with chlorine dioxide. In contrast, acesulfame potassium consumed all of the chlorine dioxide within about the first hour. These data are fairly representative of the behavior of the majority of additives that were evaluated. That is, chlorine dioxide either reacts almost immediately with an ingredient or it tends to persist over the 8 hour period with only a gradual decline.

The sucralose data (hollow squares) depicted in FIG. 1A are summarized in Table 1 to illustrate how the % decrease in chlorine dioxide was calculated. The chlorine dioxide present at 8 hours was calculated by interpolation of the data at 0.88 hours and 15.35 hours. The interpolation resulted in 166.5 ppm at 8 hours. The % decrease was then calculated using the data at 0.25 hours as $[ClO_2]_{t=initial}$. The data in Table 1 are depicted in the graph in FIG. 1B, in addition to the control.

TABLE 1

| Time (hours) | Chlorine dioxide (ppm) |
|---|---|
| 0.25 | 183 |
| 0.88 | 168 |
| 15.35 | 165 |

TABLE 1-continued

| Time (hours) | Chlorine dioxide (ppm) |
|---|---|
| 22.62 | 165 |
| 70.58 | 163 |

Multiple individual compounds were evaluated for $ClO_2$ compatibility. The results show that the compounds fall generally into two categories: those which cause no more than a 13% decrease in chlorine dioxide at 8 hours after preparation of the test sample, and those that cause at least about 30% decrease in chlorine dioxide at 8 hours. Those compounds that cause no more than a 13% decrease in chlorine dioxide were deemed compatible. Of the individual additives evaluated, 24 compounds were compatible. The chemical structure of these compounds is depicted in FIGS. 2A-2H, and the data for them is summarized in Table 2.

TABLE 2

| Comp. | Name | Function | Chemical formula | Solubility[1] | Test Method[2] | Ingredient conc. (wt. %) | $ClO_2$ decrease @ 8 hrs | Note |
|---|---|---|---|---|---|---|---|---|
| 1 | L-menthol | Flavor | $C_{10}H_{20}O$ | N | T | 0.511 | 1% | Saturated, cyclic alcohol |
| 2 | Benzaldehyde | Flavor | $C_7H_6O$ | N | T | 0.999 | 1% | Aromatic aldehyde |
| 3 | Camphor | Flavor | $C_{10}H_{16}O$ | N | T | 0.500 | 2% | Saturated, Bicyclic Ketone |
| 4 | Menthone | Flavor | $C_{10}H_{18}O$ | N | T | 1.004 | 4% | Saturated, Cyclic Ketone |
| 5 | Ethyl Menthane Carboxamide | Flavor | $C_{13}H_{25}NO$ | N | T | 0.399 | 5% | Saturated, Cyclic Carboxamide |
| 6 | Eucalyptol | Flavor | $C_{10}H_{18}O$ | N | T | 1.011 | 13% | Saturated, Bicyclic Ether |
| 7 | Aspartame | Sweetener | $C_{14}H_{18}N_2O_5$ | Y | A | 0.505 | 2% | Methyl ester of dipeptide of aspartic acid and phenylalanine |
| 8 | Sodium cyclamate | Sweetener | $C_6H_{11}NSO_3Na$ | Y | A | 0.501 | 3% | Sodium cyclohexane sulfamate |
| 9 | Sodium saccharin Dihydrate | Sweetener | $C_7H_4NNaO_3S \cdot 2H_2O$ | Y | A | 0.588 | 3% | 1,1-Dioxo-1,2-benzothiazol-3-one |
| 10 | Sucralose | Sweetener | $C_{12}H_{19}Cl_3O_8$ | Y | A | 0.518 | 9% | 1',4,6'-Trichlorogalacto-sucrose |
| 11 | Cetylpyridinium Chloride | Antiseptic | $C_{21}H_{38}NCl$ | Y | A | 0.100 | 4% | Aromatic, Quaternary Ammonium salt |
| 12 | Benzyl Alcohol | Preservative | $C_7H_8O$ | Y | A | 0.100 | 8% | Aromatic alcohol |
| 13 | Propylene Glycol | Carrier | $C_3H_8O_2$ | Y | A | 1.140 | 1% | Diol |
| 14 | Polyethylene Glycol 400 | Carrier | $HO(C_2H_4O)_nH$ | Y | A | 0.885 | 1% | Polyether diol |
| 15 | Glycerol | Carrier | $C_3H_8O_3$ | Y | A | 1.042 | 1% | Triol |
| 16 | Ethyl Acetate | Carrier | $C_4H_8O_2$ | N | T | 1.008 | 3% | Ester |
| 17 | Ethanol | Carrier | $C_2H_6O$ | Y | A | 1.098 | 4% | Primary alcohol |
| 18 | Hydroxypropyl Methylcellulose | Thickener | (see FIG. 2G) | Y | T | 0.408 | 2% | Polymeric carbohydrate with methyl and hydroxypropyl ether groups; nonionic |
| 19 | Acetone | Solvent | $C_3H_6O$ | Y | A | 1.247 | 0.04% | Ketone |
| 20 | Glycine | Buffer | $C_2H_5NO_2$ | Y | A | 0.096 | 2% | Amino acid |
| 21 | l-Glutamic Acid | Buffer | $C_5H_9NO_4$ | Y | A | 0.096 | 1% | Amino acid |
| 22 | Boric Acid | Buffer | $H_3BO_3$ | Y | A | 0.096 | 1% | Inorganic acid |

TABLE 2-continued

| Comp. | Name | Function | Chemical formula | Solubility[1] | Test Method[2] | Ingredient conc. (wt. %) | $ClO_2$ decrease @ 8 hrs | Note |
|---|---|---|---|---|---|---|---|---|
| 23 | Citric Acid | Buffer | $C_6H_8O_7$ | Y | A | 0.1 | 3% | Trifunctional Organic Acid |
| 24 | Sodium Bisulfate | Buffer | $NaHSO_4$ | Y | A | 0.1 | 2% | Inorganic Acid |

[1] Solubility in water.
[2] T = titration method. A = absorption method.

The chemical structures of the compounds that cause at least about a 30% decrease in chlorine dioxide at 8 hours are shown in FIGS. 3A-3F. The data for them are summarized in Table 3. Analysis of the chemical structures of the compounds that cause at least a 30% decrease in chlorine dioxide revealed certain chemical moieties that are suspected to react with chlorine dioxide. The suspected moieties are conjugated double bounds excluding the conjugated bond found in aromatic rings (t-cinnamaldehyde, furaneol, ascorbic acid, sorbic acid, acesulfame potassium, and potassium sorbate); oxygen atoms adjacent to aromatic rings ("phenolic-type" oxygen, including ether oxygen; methyl vanillin, anethole, and phenol), ionized salts of carboxylic acids (potassium acetate, sodium propionate, potassium sorbate and sodium carboxymethylcellulose), amino-ethanols (R1-N—$CH_2$—$CH_2$—OH; triethanolamine and monoethanolamine), and inorganic carbonate salts ($XCO_3$; sodium carbonate). Chemical moieties present in the compatible additives include but are not limited to: saturated and cyclic hydrocarbons, aromatics, non-ionized non-aromatic carboxylic acids, amines, ethers, aldehydes, ketones, alcohols, and quaternary ammonium salts.

TABLE 3

| Comp. | Name | Function | Chemical formula | Solubility[1] | Test Method[2] | Ingredient conc. (wt. %) | $ClO_2$ decrease @ 8 hrs | Note |
|---|---|---|---|---|---|---|---|---|
| 25 | Potassium Acetate | Flavor | $C_2H_3O_2K$ | Y | A | 1.00 | 30% | Simple salt of an organic acid |
| 26 | t-Cinnamaldehyde | Flavor | $C_9H_8O$ | N | T | 1.015 | 37% | Aromatic aldehyde with a conjugated C=C double bond |
| 27 | Furaneol | Flavor | $C_6H_8O_3$ | N | T | 0.408 | 100% | Cyclic ether with conjugated carbon-carbon double bond, with alcohol and ketone functionality |
| 28 | Ascorbic Acid | Flavor | $C_6H_8O_6$ | Y | A | 0.408 | 100% | Cyclic acid with conjugated carbon-carbon double bond, with multiple alcohol groups |
| 29 | Sorbic Acid | Flavor | $C_6H_8O_2$ | N | T | 1.015 | 100% | Linear acid with conjugated carbon-carbon double bond |
| 30 | Methyl Vanillin | Flavor | $C_8H_8O_3$ | Y | T | 0.404 | 100% | Aromatic alcohol, ether and aldehyde |
| 31 | Anethole | Flavor | $C_{10}H_{12}O$ | N | T | 1.016 | 100% | Aromatic ether |
| 32 | Acesulfame Potassium | Sweetener | $C_4H_4NO_4SK$ | Y | A | 0.505 | 100% | Potassium 6-methyl-2,2-dioxo-oxathiazin-4-olate |
| 33 | Phenol | Antiseptic | $C_6H_6O$ | Y | T | 0.100 | 100% | Aromatic alcohol |
| 34 | Sodium Propionate | Preservative | $C_3H_5O_2Na$ | Y | A | 0.100 | 44% | Simple salt of an organic acid |
| 35 | Potassium Sorbate | Preservative | $C_7H_5O_2K$ | Y | A | 0.100 | 99% | Simple salt of a conjugated organic acid |
| 36 | Sodium Carboxymethylcellulose | Thickener | (see FIG. 3E) | Y | T | 1.90 | 13% | Polymeric carbohydrate with partially ionized acid groups; anionic |
| 37 | Triethanolamine | Buffer | $C_6H_{15}NO_3$ | Y | A | 0.096 | 96% | Trifunctional Aminoethanol |
| 38 | Monoethanolamine | Buffer | $C_2H_7NO$ | Y | A | 0.096 | 92% | Monofunctional Aminoethanol |
| 39 | Sodium Carbonate | Buffer | $Na_2CO_3$ | Y | A | 0.096 | 85% | Inorganic Base |

[1] Solubility in water.
[2] T = titration method. A = absorption method.

While not wishing to be bound by theory, it is thought that the relatively increased reactivity of ionized carboxylic acid with chlorine dioxide compared to that of non-ionized carboxylic acid may be related to the ability of the non-ionized version to form acid dimers due to hydrogen bonding, as shown here:

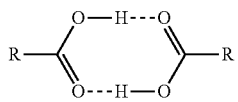

Sodium carboxylic methylcellulose contains ionized carboxylic acid moieties, yet has a relatively low decrease in chlorine dioxide at 8 hours. Without wishing to be bound by theory, it is believed that the tertiary structure of the NaCMC polymer is affected by pH, because as the pH is lowered, more of the COO— becomes COOH. The pH of the compositions tested in this Example had a pH of about 5; this is a fairly low pH for NaCMC. It is believed that a change in tertiary structure could alter the accessibility of the ionized carboxylic groups and thereby reduce the NaCMC polymer's apparent reactivity with the chlorine dioxide.

To examine the compatibility of a composition comprising multiple compatible additives and a compatible amount of a non-compatible additive, the composition shown in Table 4 was prepared.

TABLE 4

Composition 34

| Ingredient | Concentration (wt. %) |
|---|---|
| Water | 95.5 |
| Sodium Carboxymethylcellulose | 2.83 |
| ASEPTROL ® S-Tab2 | 0.8 |
| Menthol | 0.4 |
| Propylene Glycol | 0.4 |
| Sucralose | 0.1 |

The composition was prepared as follows. First, 1.41 grams of menthol crystals were dissolved in an equal mass of propylene glycol in a vial. Then 9.99 grams of NaCMC powder were then added to 221.84 grams of water in a jar. The NaCMC powder was allowed to hydrate overnight. After remixing the NaCMC-water mixture to a uniform consistency, 0.353 grams of sucralose were added to the gel. The gel was mixed until all of the sucralose powder was dissolved. The menthol propylene glycol solution was then added to the gel and thoroughly mixed by hand using a spatula. Six (6.00) grams of the gel was then loaded into a 10-cc syringe. To prepare a concentrated ClO2 solution, a 240 mg S-Tab2 tablet was load into a second 10 cc syringe, and 9.76 grams of de-ionized water was then dispensed into the syringe containing the tablet. The tablet was allowed to react for 10 minutes without any agitation. After 10 minutes, all of the ClO$_2$ had evolved from the tablet, and the syringe was inverted several times to incorporate any undissolved portion of the tablet into solution. The ClO$_2$ concentrate was then mixed with the gel by attaching the two 10 cc syringes together using a LuerLok union. The plungers were depressed in a alternating fashion to transfer the mixture back and forth through the syringe union. About 40 depressions was sufficient to produce a homogenous gel having a nominal concentration of 200 ppm ClO$_2$ The chlorine dioxide concentration of Comp. 34 was assessed by titration. The data for Comp. 34 are shown graphically in FIG. 4. Data for the individual components are also shown in FIG. 4. The decrease in chlorine dioxide for Composition 34 is just under 50% at 8 hours. The decrease remains substantially stable at about 50% for over 70 hours. The data show that the decrease in chlorine dioxide due to the different additives is approximately cumulative.

Composition 34 was assessed for cytotoxicity as per the United States Pharmacopeia (USP) biological reactivity limits of the Agar Diffusion Test of USP <87> "Biological Reactivity, in vitro," (approved protocol current in 2007). Composition 34 was found to be non-cytotoxic.

A method of whitening teeth using Comp. 34 is contemplated. The method will be carried out by contacting a tooth surface with Comp. 34 within about 8 hours after Comp. 34 is prepared or within about 1 hour after preparation. The duration of contact will be between about 10 to about 30 minutes. A second episode of contacting the tooth surface with Comp. 34 is performed; the second episode occurs within about 30 minutes of the completion of the first episode of contact. The duration of the second episode of contact will also be between about 10 to about 30 minutes. It is further contemplated that the composition for the second episode with be freshly prepared prior to its use in the method.

The disclosures of each and every patent, patent application, and publication cited herein are hereby incorporated herein by reference in their entirety.

While the compositions, kits, and their methods of use have been disclosed with reference to specific embodiments, it is apparent that other embodiments and variations may be devised by others skilled in the art without departing from the true spirit and scope of the described compositions, kits and methods of use. The appended claims are intended to be construed to include all such embodiments and equivalent variations.

What is claimed is:

1. A composition consisting of:
    (i) about 150 parts-per-million (ppm) to about 2000 ppm chlorine dioxide, optionally components in minute quantities derived from chlorine-dioxide forming reactants, and no more than about 0.25 milligrams (mg) oxy-chlorine anion per gram composition,
    (ii) an aqueous vehicle,
    (iii) at least one compatible additive wherein the at least one compatible additive has a chemical structure selected from the group consisting of a saturated hydrocarbon, a cyclic hydrocarbon, an aromatic, a non-ionized non-aromatic carboxylic acid, an amine, an ether, an aldehyde, a ketone, an alcohol, a quaternary ammonium salt and combinations thereof, wherein no compatible additive comprises any of a conjugated double bond, an oxygen atom adjacent to an aromatic ring, an ionized salt of carboxylic acid, an amino-ethanol and an inorganic carbonate salt, and
    (iv) optionally a compatible amount of at least one non-compatible additive, wherein the at least one non-compatible additive is selected from the group consisting of a simple salt of an organic monocarboxylic acid that does not comprise a conjugated double bond, an aromatic aldehyde with a conjugated C=C double bond, and a polymeric carbohydrate with partially ionized acid groups, wherein a compatible amount refers to a concentration of the non-compatible additive at which no more than about 45% decrease in chlorine dioxide occurs after 8 hours.

2. The composition of claim 1, wherein the at least one compatible additive is selected from the group consisting of a sweetener, a carrier, a flavor agent, an antiseptic, a preservative, a pigment, a fragrance, a plasticizer, an encapsulate, an antitartar agent, a surfactant, a buffer, and a cleaning agent.

3. The composition of claim 1, wherein the at least one compatible additive is selected from the group consisting of: L-menthol, benzaldehyde, camphor, methone, ethyl methane carboxamide, eucalyptol, aspartame, sodium cyclamate, sodium saccharin dihydrate, sucralose, cetylpyridinium chloride, benzoyl alcohol, propylene glycol, polyethylene glycol 400, glycerol, ethyl acetate, ethanol, hydroxypropyl methylcellulose, acetone, glycine, l-glutamic acid, boric acid, citric acid, and sodium bisulfate.

4. The composition of claim 1, wherein a non-compatible additive is present and is a thickener.

5. The composition of claim 1, wherein the composition contains a first compatible additive and a second compatible additive.

6. The composition of claim 5, wherein the first compatible additive is a sweetener and the second compatible additive is a flavor agent.

7. The composition of claim 5, wherein a non-compatible additive is present.

8. The composition of claim 6, wherein a non-compatible additive is present.

9. The composition of claim 8, wherein the non-compatible additive is sodium carboxymethylcellulose.

10. The composition of claim 6, wherein the sweetener is present at about 0.5 wt. % to about 1.0 wt, % and the flavor agent is present at about 0.4 wt, % to about 1.1 wt. %.

11. The composition of claim 1, wherein the chlorine dioxide is prepared from a substantially anhydrous solid body comprising particulate reagents, wherein the reagents comprise a sodium chlorite, sodium bisulfate and optionally dichloroisocyanuric acid or a hydrate thereof.

12. The composition of claim 1, wherein the composition has an ionic strength of at least about 5% of the chlorine dioxide in the composition.

13. A method of preparing a chlorine-dioxide containing composition containing a compatible additive, said method comprising the step of:
  combining: (i) a chlorine dioxide precursor in the form of a substantially anhydrous solid body comprising particulate reagents, wherein the reagents comprise a sodium chlorite, sodium bisulfate and optionally dichloroisocyanuric acid or a hydrate thereof, (ii) at least one compatible additive, wherein the at least one compatible additive has a chemical structure selected from the group consisting of a saturated hydrocarbon, a cyclic hydrocarbon, an aromatic, a non-ionized non-aromatic carboxylic acid, an amine, an ether, an aldehyde, a ketone, an alcohol, a quaternary ammonium salt and combinations thereof, wherein no compatible additive comprises any of a conjugated double bond, an oxygen atom adjacent to an aromatic ring, an ionized salt of carboxylic acid, an amino-ethanol and an inorganic carbonate salt, (iii) optionally a compatible amount of at least one non-compatible additive, wherein the at least one non-compatible additive is selected from the group consisting of a simple salt of an organic monocarboxylic acid that does not comprise a conjugate double bond, an aromatic aldehyde with a conjugated C=C double bond, and a polymeric carbohydrate with partially ionized acid groups, wherein a compatible amount refers to a concentration of the non-compatible additive at which no more than about 45% decrease in chlorine dioxide occurs after 8 hours, and (iv) an aqueous vehicle,
  thereby preparing a composition consisting of about 150 parts-per-million (ppm) to about 2000 ppm chlorine dioxide, optionally components in minute quantities derived from the chlorine-dioxide forming particulate reactants, no more than about 0.25 milligrams (mg) oxychlorine anion per gram composition, and a compatible additive.

14. A method of whitening a tooth surface, the method comprising contacting a surface of a tooth with an efficacious amount of a composition according to claim 1.

15. The method of claim 14, wherein contacting the tooth surface with the composition does not: substantially damage hard tooth tissue, substantially reduce enamel microhardness, substantially reduce dentin microhardness, cause tooth sensitivity, and/or substantially increase surface roughness of at least one of enamel and dentin.

16. The method of claim 14, wherein the step of contacting the tooth surface results in substantial contact of the composition with soft oral tissues.

17. The method of claim 14, wherein said contacting step is iterated at least once, resulting in a first iteration and a second iteration.

18. The method of claim 14, wherein the at least one compatible additive is selected from the group consisting of: a sweetener, a carrier, a flavor agent, an antiseptic and a preservative.

19. The method of claim 18, wherein a compatible amount of a non-compatible additive is present, wherein the non-compatible additive is a thickener.

20. The composition of claim 1, wherein at least one non-compatible additive is present at a concentration at which no more than about 30% decrease in chlorine dioxide occurs after 8 hours.

* * * * *